(12) United States Patent
Lough

(10) Patent No.: US 10,926,001 B2
(45) Date of Patent: *Feb. 23, 2021

(54) METHODS RELATED TO MINIMALLY POLARIZED FUNCTIONAL UNITS

(71) Applicant: POLARITYE, INC., Salt Lake City, UT (US)

(72) Inventor: Denver M. Lough, Baltimore, MD (US)

(73) Assignee: PolarityTE, Inc., Salt Lake City, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 14/954,335

(22) Filed: Nov. 30, 2015

(65) Prior Publication Data

US 2016/0151540 A1 Jun. 2, 2016

Related U.S. Application Data

(60) Provisional application No. 62/086,526, filed on Dec. 2, 2014.

(51) Int. Cl.
| | | |
|---|---|---|
| *C12N 5/071* | (2010.01) | |
| *A61L 27/38* | (2006.01) | |
| *A01N 1/02* | (2006.01) | |
| *A61L 27/54* | (2006.01) | |

(52) U.S. Cl.
CPC .......... *A61L 27/3813* (2013.01); *A01N 1/021* (2013.01); *A01N 1/0221* (2013.01); *A61L 27/54* (2013.01); *C12N 5/0625* (2013.01); *A61L 2300/412* (2013.01); *A61L 2430/00* (2013.01); *C12N 2513/00* (2013.01)

(58) Field of Classification Search
None
See application file for complete search history.

(56) References Cited

U.S. PATENT DOCUMENTS

| | | |
|---|---|---|
| 9,592,257 B2 | 3/2017 | Wu |
| 9,655,930 B2 | 5/2017 | Wu |
| 9,737,570 B2 | 8/2017 | Lin |
| 2006/0134074 A1 | 6/2006 | Naughton |
| 2006/0240555 A1 | 10/2006 | Ronfard |
| 2009/0012536 A1 | 1/2009 | Rassman et al. |
| 2009/0280095 A1 | 11/2009 | Szabowski et al. |
| 2011/0076303 A1 | 3/2011 | Iwabuchi et al. |
| 2012/0196312 A1 | 8/2012 | Sato et al. |
| 2013/0101564 A1 | 4/2013 | Chen |
| 2013/0189327 A1 | 7/2013 | Ortega et al. |
| 2014/0044713 A1 | 2/2014 | De Lau et al. |
| 2014/0106447 A1 | 4/2014 | Brown et al. |

FOREIGN PATENT DOCUMENTS

| | | |
|---|---|---|
| EP | 2 412 800 A1 | 2/2012 |
| JP | 2014-516562 A | 7/2014 |
| WO | 2006008009 A2 | 1/2006 |
| WO | 2010/112678 A1 | 10/2010 |
| WO | 2012/168930 A2 | 12/2012 |
| WO | WO-2013/060899 A2 | 5/2013 |
| WO | 2014059027 A1 | 4/2014 |
| WO | 2014159356 A1 | 10/2014 |

OTHER PUBLICATIONS

Sugihari et al., Reconstruction of the skin in three-dimensional collagen gel matrix culture, In Vitro Cell. Dev. Biol., 27A:142-146, Feb. 1991.*
Biedermann et al., Human Eccrine Sweat Gland Cells CAn Reconstitute a Stratified Epidermis, Journal of Investigative Dermatology, 2010, vol. 130, pp. 1996-2009.*
Gao et al., Isolation, culture and phenotypic characterization of human sweat gland epithelial cells, International Journal of Moledular Medicine, 34: 997-1003, 2014.*
Dictionary.com/cornification, retrieved from the internet: http://www.dictionary.com/browse/cornification, Jun. 3, 2018.*
Lee et al., Tissue Engineering: Part C, vol. 17, No. 4, 2011, pp. 391-400.*
Limat et al., The Journal of Investigative Dermatology, vol. 87, pp. 485-488, 1986.*
Ohyama et al., Dermatology, 2007; 214: 342-351.*
Stenn et al., Current Opinion in Biotechnology, 2005, vol. 16:493-497.*
Wong et al., International Journal of Biomaterials, vol. 2012, Article ID 926059, 8 pages.*
Zanzottera et al., Journal of Cosmetics, Dermatological Sciences and Applications, 2014, 4, 268-274.*
Snippert et al., Lgr6 Marks Stem Cells in the Hair Follicle That Generate All Cell Lineages of the Skin, Science Magazine, Mar. 12, 2010, Supporting Online Material, 23 pages.*
Chang et al., PNAS Mar. 5, 2013 110 (10) E908-E917, published online Feb. 19, 2013, retrieved from the internet Apr. 18, 2019: https://www.pnas.org/content/110/10/E908.*
Mbinfo et al., What is cell polarity?, retrieved from the internet Apr. 18, 2019: https://www.mechanobio.info/development/what-is-cell-polarity/.*
Gabel Hair Restoration, The Hair Follicle Anatomy, Oct. 15, 2016, retrieved from the Internet: www.gabelcenter.com/anatomy-hair-follicle/ (Year: 2016).*

(Continued)

*Primary Examiner* — Scott Long
*Assistant Examiner* — Evelyn Y Pyla
(74) *Attorney, Agent, or Firm* — Crowell & Moring LLP; Mary R. Bram; Deborah H. Yellin

(57) ABSTRACT

Provided herein are constructs of micro-aggregate multicellular, minimally polarized grafts containing Leucine-rich repeat-containing G-protein coupled Receptor (LGR) expressing cells for wound therapy applications, tissue engineering, cell therapy applications, regenerative medicine applications, medical/therapeutic applications, tissue healing applications, immune therapy applications, and tissue transplant therapy applications which preferably are associated with a delivery vector/substrate/support/scaffold for direct application.

30 Claims, 23 Drawing Sheets

(56) References Cited

OTHER PUBLICATIONS

Adanali et al., Aesthetic Plastic Surgery, 26:465-469, 2002 (Year: 2002).*
Uebel et al., The Punctiform Technique in Hair Transplantation, Seminars in Plastic Surgery, vol. 19, No. 2, 2005, pp. 109-127 (Year: 2005).*
Gho et al., Improved hair restoration method for burns, BURNS 37 (2011) 427-433 (Year: 2011).*
International Application No. PCT/US2015/063114, Notification of Transmittal of the International Search Report and the Written Opinion of the International Searching Authority, or the Declaration, dated Mar. 4, 2016.
Lough et al.: "Development of a Chimeric Free Flap Allograft Using the LGR6+ Epithelial Stem Cell," Plastic Reconstructive Surgery, Mar. 2014, vol. 133 (3 Suppl), pp. 120-121, Abstract Only.
Andi, T., Reddy, S., Gaddapara, T., Millar, S.: "WNT Signals Are Required for the Initiation of air Follicle Development," Department of Dermatology and Cell and Developmental Biology, May 2002, pp. 643-653. vol. 2, Cell Press, Philadelphia.
Balwierz, A., et al.: "Human adipose tissue stromal vascular fraction cells differentiate depending on distinct types of media", Collegium Medicum Jagiellonian University Journal compilation, 2008, pp. 441-459, 41, Blackwell Publishing Ltd., Poland.
Barker, N., and Clevers, H. :"Leucine-Rich Repeat-Containing G-Protein-Coupled Receptors as Markers of Adult Stem Cells," Reviews in Basic and Clinical Gastroenterology, 2010, pp. 1681-1969, 138, Netherlands.
Bevins, C., and Salzman, N.:"Paneth cells, antimicrobial peptides and maintenance of intestinal homeostasis", Nature Journal, May 2011, pp. 356-368, vol. 9, Macmillan Publishers Limited, United States.
Bick, R., et al.:"Nucelar Localization of HBD-1 in Human Keratinocytes," Journal of Burns and Wounds, Aug. 24, 2007, pp. 25-32, United States.
Blanpain, C.,:"Skin regeneration and repair," Nature Journal, Apr. 2010, pp. 686-687, vol. 464, Macmillan Publishers Limited, United States.
Brayfield, C., Mara, J., and Rubin, P.:"Adipose Stem Cells for Soft Tissue Regeneration," Review, 2010, 42, pp. 124-128, Pittsburgh.
Castilho, R., et al.: "mTOR Mediates Wnt-Induced Epidermal Stem Cell Exhaustion and Aging," Cell Stem Cell, Sep. 4, 2009, 5(3), pp. 279-289, NIH Public Access.
Cherubino, M, et al.: "Adipose-Derived Stem Cells for Wound Healing Applications" Review Article: Annals of Plastic Surgery, Feb. 2011, pp. 210-215, vol. 66, No. 2, Lippincott Williams & Wilkins.
Cushing, G., and Phillips, L.: "Evidence-Based Medicine: Pressure Sores" Plastic Reconstruction Surgery Journal, 2013, pp. 1720-1732, 132, American Society of Plastic Surgeons.
D'Amigo, R. et al.: "A Report of the ASPS Task Force on Regenerative Medicine: Opportunities for Plastic Surgery," Plastic Reconstruction Surgery Journal, 2013, pp. 393-399, 131, American Society of Plastic Surgeons.
Heagebarth, A., and Clevers, H.: "Wnt Signaling, Lgr5, and Stem Cells in the Intestine and Skin," The American Journal of Pathology, Mar. 2009, pp. 715-721, vol. 174, No. 3, American Society for Investigative Pathology, Netherlands.
Hirose, K., Shimoda, N., and Kikuchi, Y.: "Expression patterns of lgr4 and lgr6 during zebrafish development," Gene Expression Patterns, 2011, pp. 378-383, 11, Elsevier.
Horsley, V.: "Upward bound: follicular stem cell fate decisions," The European Molecular Biology Organization Journal, 2011, pp. 2986-2987, vol. 30, No. 15, European Molecular Biology Organization.
Hsu, S., et al.: "Characterization of Two LGR Genes Homologous to Gonadotropin and Thyrotropin Receptors with Extracellular Leucine-Rich Repeats and a G Protein-Coupled, Seven-Transmembrane Region," Journal of Molecular Endocrinology, 1998, pp. 1830-1845, The Endocrine Society.

Ito, M., et al.: "Wnt-dependent de novo hair follicle regeneration in adult mouse skin after wounding," Nature Journal, 2007, pp. 316-320, vol. 447, Nature Publishing Group.
Jinno, H., et al.: "Convergent Genesis of an Adult Neural Crest-Like Dermal Stem Cell from Distinct Developmental Origins," Stem Cells, 2010, pp. 2027-2040, 28.
Klar, A. et al.: "Tissue-engineered derma-epidermal skin grafts prevascularized with adipose-derived cells," Biomatenals, 2014, pp. 5065-5078, 35, Elsevier Limited.
Kokai, L., Marra, K., and Rubin, J.: "Adipose stem cells: biology and clinical applications for tissue repair and regeneration," 2014, pp. 399-408.
Leushacke, M., and Barker, N.:"Lgr5 and Lgr6 as markers to study adult stem cell roles in self-renewal and cancer," Nature Journal, 2012, pp. 3009-3022, 31, Macmillan Publishers Limited.
Levy, V., et al.: "Distinct Stem Cell Populations Regenerate the Follicle and Interfollicular Epidermis," Developmental Cell, Dec. 2005, pp. 855-861, vol. 9, Elsevier Inc.
Levy, V., et al.: "Epidermal stem cells arise from the hair follicle after wounding," The FASEB Journal, 2007, pp. 1358-1366.
Li, H., et al.: "Adipogenic Potential of Adipose Stem Cell Subpopulations", Plastic Reconstruction Surgery Journal, 2011, pp. 663-672, 128, The American Association of Plastic Surgeons.
Lin, C., et al.: "Defining adipose tissue-derived stem cells in tissue and culture", Histology and Histopathology, 2010, pp. 807-815, No. 25.
Lough, D., et al.: Abnormal CX3CR1 Lamina Propria Myeloid Cells From Intestinal Transplant Recipients with NOD2 Mutations, American Journal of Transplantation, 2012, pp. 992-1003, 12, The American Society of Transplantation and the American Society of Transplant Surgeons.
Lough, D., et al.: "Stimulation of the Follicular Bulge LGR5 and LGR6 Stem Cells with the Gut-Derived Human Alpha Defensin 5 Results in Decreased Bacterial Presence, Enhanced Wound Healing, and Hair Growth from Tissues Devoid of Adnexal Structures", Plastic Reconstruction Surgery Journal, 2013. p. 1159-1171, 132, American Society of Plastic Srugeons.
Lough, D., et al.: "Transplantation of the LGR6 Epithelial Stem Cell into Full-Thickness Cutaneous Wounds Results in Enhanced Healing, Nascent Hair Follicle Development, and Augmentation of Angiogenic Analytes", Plastic Reconstruction Surgery Journal, 2014, pp. 579-590, 133, American Society of Plastic Surgeons.
Milner, S., and Ortega, M.: "Recued antimicrobial peptide expression in human burn wounds", Burns, 1999, pp. 411-413, Elsevier Science Ltd., United States.
Nath, M., Offer, M., and Hummel, M.: "Isolation and in vitro expansion of lgr6-positive multipotent hair follicle stem cells", Cell Tissue Res, 2011, pp. 435-444, 344, Springer-Verlag, Germany.
Niyonsaba, F., and Ogawa, H., "Protective roles of the skin against infection: Implication of naturally occurring human antimicrobial agents [Beta]-defensins, cathelicidin LL-37 and lysozyme", Journal of Dermatological Science, 2005, pp. 157-168, 40, Elsevier Ireland Ltd.
Niyonsaba, F., et al.: "Antimicrobial Peptides Human [Beta]-Defensins Stimulate Epidermal Keratinocyte Migration, Proliferation and Production of Proinflammatory Cytokines and Chemokines", Journal of Investigative Dermatology, 2007, pp. 594-604, 127.
Oppenheim, J., and Yang, D.: "Alarmins: chemotactic activators of immune responses", Current Opinion in Immunology, 2005, pp. 359-365, 17, Elsevier.
Ortega, M., Ganz, T., Milner, S.: "Human beta defensin is absent in burn blister fluid", Burns, 2000, pp. 724-726, 26, Elsevier.
Otte, J., et al.: "Human Beta Defensin2 Promotes Intestinal Wound Healing in Vitro", Journal of Cellular Biochemistry, 2008, pp. 2286-2297, 104, Wiley-Liss Inc.
Rubin, P., and Marra, K.: "Soft Tissue Reconstruction", Methods in Molecular Biology, 2011, pp. 395-400, Springer Science and Media, LLC.
Planat-Bernard, V., et al.: "Plasticity of Human Adipose Lineage Cells Toward Endothelial Cells Physiological and Therapeutic Perspectives", Circulation American Heart Association Journal, 2004, pp. 656-663, 109.

(56) References Cited

OTHER PUBLICATIONS

Sato, T., et al.: "Single Lgr5 stem cells build crypt-villus structures in vitro without a mesenchymal niche", Nature, May 14, 2009, p. 262-265, vol. 459, Macmillan Publishers Limited.
Schauber, J., and Gallo, R.: "Antimicrobial peptides and the skin immune defense system", Journal of Allergy Clinical Immunology, 2008, pp. 261-266, 122, American Academy of Allergy, Asthma & Immunology.
Sorensen, O., et al.: "Injury-induced innate immune response in human skin mediated by transactivation of the epidermal growth factor receptor", The Journal of Clinical Investigation, Jul. 2006, pp. 1878-1885, vol. 116, No. 7.
Sheng, L., et al.: "Transplantation of stromal vascular fraction as an alternative for accelerating tissue expansion", The International Journal of Surgical Reconstruction, 2013, pp. 551-557, 66, Elsevier.
Sieber-Blum, M., and Grim, M.: "The Adult Hair Follicle: Cradle for Pluripotent Neural Crest Stem Cells", Birth Defects Research (Part C), 2004, pp. 162-172, 72, Wiley-Liss Inc.
Snippert, H., et al.: "Lgr6 Marks Stem Cells in the Hair Follicle That Generate All Cell Lineages of the Skin", Science Magazine, Mar. 12, 2010, p. 1385-1388, 327.
Tsuji, W., Rubin, P., and Marra, K.: "Adipose-derived stem cells: Implications in tissue regeneration", World Journal of Stem Cells, Jul. 26, 2014, pp. 312-321, vol. 6, No. 3, Baishideng Publishing Group Inc.
Tumbar, T.: "The ontogeny of epithelial skin stem cells", National Institute of Health Public Access, Jul. 2014.
Wang, H., et al.: "Effect of human beta-defensin-3 on the proliferation of fibroblasts on periodontally involved root surfaces", Peptides, 2011, pp. 888-894, No. 32.
White, S., Wimley, W., and Selsted, M.: "Structure, function, and membrane integration of defensins", Current Opinion in Structural Biology, 1995, pp. 521-527, 5.
Zasloff, M.: "Antimicrobial Peptides in Health and Disease" The New England Journal of Medicine, Oct. 10, 2002, vol. 347, No. 15, p. 1199-1200, Massachusetts Medical Society.
Zong, Z., et al.: "Effect of hBD2 Genetically Modified Dermal Multipotent Stem Cells on Repair of Infected Irradiated Wounds", Journal of Radiation Research, 2010, pp. 573-580, 51.
Messerli, Mark et al. "Extracellular Electrical Fields Direct Wound Healing and Re-generation," Biol. Bull. 221: 79-92.
Zallen, Jennifer, "Planar Polarity and Tissue Morphogenesis," Cell 129, Jun. 15, 2007, pp. 1051-1063.
Asselineau, D. et al., Human Epidermis Reconstructed by Culture: Is It "Normal"? J Invest Dermatol 86:181-186, 1986.
Boyce, S.T., et al., Biologic attachment, growth and differentiation of cultured human epidermal keratinocytes on a graftable collagen and chondroitin-6-sulfate substrate, Surgery 4:421-431, 1988.
Snippert, H.J., et al. Tracking adult stem cells, EMBO Reports, 12(2)113-122.
Pomahac, B., et al., Tissue Engineering of Skin, Crit Rev Oral Biol Med, 9(3):333-344, 1998.
Takami, Y., et al., Clinical Application and Histological Properties of Autologous Tissue-engineered Skin Equivalents Using an Acellular Dermal Matrix, J Nippon Med Sch, 81:356-363, 2014.
Barker, N. e tal., Lgr proteins in epithelial stem cell biology, Development 140:2484-2494, 2013.
Shamir et al., "Three-dimensional organotypic culture: experimental models of mammalian biology and disease", Nature Reviews Molecular Cell Biology, vol. 15, Oct. 2014, pp. 647-664.
Morris et al., "Capturing and profiling adult hair follicle stem cells", Nature Biotechnology, vol. 22, No. 4, Apr. 2004, pp. 411-417.
Extended European Search Report for Application No. 15865131.5 dated Dec. 4, 2018.
Koh-ei Toyoshima et al., "Fully functional hair follicle regeneration through the rearrangement of stem cells and their niches", Nature Communications, 3:784, published Apr. 17, 2012, 12 pages.
Sato et al., "Growing Self-Organizing Mini-Guts from a Single Intestinal Stem Cell: Mechanism and Applications", Science, vol. 340, Jun. 7, 2013, pp. 1190-1194.

Asakawa et al., "Hair organ regeneration via the bioengineered hair follicular unit transplantation", Scientific Reports, 2:424, published May 28, 2012, 7 pages.
Zografou et al., "Improvement of skin-graft survival after autologous transplantation of adipose-derived stem cells in rats," Journal of Plastic, Reconstructive & Aesthetic Surgery (2011) 64, pp. 1647-1656.
Driskell et al., "Hair follicle dermal papilla cells at a glance," J. Cell Sci., Apr. 15, 2011; 124(8): 1179-1182.
Kwon et al., "Hair Follicle Melanocyte Cells as a Renewable Source of Melanocytes for Culture and Transplantation," EPlasty, 2008; 8: e7, pp. 52-60, published online Jan. 9, 2008.
Merriam-Webster Thesaurus, Dissect; retrieved from the internet Oct. 2, 2019: https://www.merriam-webster.com/thesaurus/dissect.
Navsaria et al., "Reepithelialization of a Full-Thickness Burn from Stem Cells of Hair Follicles Micrografted into a Tissue-Engineered Dermal Template (Integra)," Plastic and Reconstructive Surgery, Mar. 2004, pp. 978-981.
Weinberg et al., "Report Reconstitution of Hair Follicle Development In Vivo: Determination of Follicle Formation, Hair Growth, and Hair Quality by Dermal Cells," The Journal of Investigative Dermatology; vol. 100, No. 3, Mar. 1993, pp. 229-236.
Yang et al., "Review of hair follicle dermal cells," J Dermatol Sci. Jan. 2010; 57(1): 2.
Zheng et al., "Isolation of Mouse Hair Follicle Bulge Stem Cells and Their Functional Analysis in a Reconstitution Assay," (2016) In: Hoffman R. (eds) Multipotent Stem Cells of the Hair Follicle. Methods in Molecular Biology, vol. 1453, p. 57-69.
Zheng et al., "Organogenesis From Dissociated Cells: Generation of Mature Cycling Hair Follicles From Skin-Derived Cells," J Invest Dermatol 124: 867-876, 2005.
Paz et al., "Challenges and Opportunities for Tissue-Engineering Polarized Epithelium," Tissue Engineering: Part B, vol. 20, No. 1, 2014, pp. 56-72.
O'Brien, "Biomaterials and Scaffolds for Tissue Engineering," *Materials Today* 14(3): 88-95 (2011).
Lee et al., "Growth factor delivery-based tissue engineering: general approaches and a review of recent developments," *J. R. Soc. Interface* 8(55): 153-170 (2011).
Lau et al., "The R-spondin/Lgr5/Rnf43 module: regulator of Wnt signal strength," *J Genes & Dev.* 28: 305-316 (Feb. 2014).
Biswas et al., "The Micrograft Concept for Wound Healing: Strategies and Applications," Journal of Diabetes Science and Technology, vol. 4, Issue 4, Jul. 2010, 808-819.
Svensjo et al., "Autologous Skin Transplantation: Comparison of Minced Skin to Other Technologies," Journal of Surgical Research 103, 19-29 (2002).
Tam et al., "Fractional Skin Harvesting: Autologous Skin Grafting without Donor-site Morbidity," PRS GO, 2013, 1-9.
Singh et al., "Challenging the Conventional Therapy: Emerging Skin Graft Techniques for Wound Healing," Plast. Reconstr. Surg. 2015;136(4):524e-530e.
Cole, "An Analysis of Follicular Punches, Mechanics, and Dynamics in Follicular Unit Extraction," Facial Plast Surg Clin N Am 21 (2013) 437-447.
Bernstein Medical, Center for Hair Restoration, ACell Extracellular Matrix for Cloning (2010) (four (4) pages).
Bassino et al., Experimental Dermatology, 2015, vol. 24, pp. 388-390, 2015.
Gabel Hair Restoration, Aug. 16, 2014, https://www.gabelcenter.com/what-is-a-follicular-unit/, accessed May 27, 2020 (five (5) pages).
http://encyclopedia.lubopitko-bg.com/structureofskin.html, accessed May 27, 2020 (three (3) pages).
Torres,Initial characterization of murine epidermal Lgr6+ stem cells, 2013, from http://repositorio.educacionsuperior.gob.ec/bitstream/28000/1324/1/T-SENESCYT-00453.pdf,pp. 1-46.
Jaks et al., "Lgr5 marks cycling, yet long-lived, hair follicle stem cells," Nat Genet, 2008; 40:1291-1299.
Chapters 1 and 6 of Hair Transplantation, The Art of Follicular Unit Micrografting and Minigrafting, 2nd Ed, (eds. Alfonso Barrera and Carlos Oscar Uebel), 2014.

(56) References Cited

OTHER PUBLICATIONS

Seager D, "Micrograft Size and Subsequent Survival," American Society for Dermatologic Surgery, Inc. Dermatol Surg 1997; 23:757-762.

Wowk, "How Cryoprotectants Work," Cryonics/Third Quarter, 2007, 3-7.

Chaytor et al., "Inhibiting ice recrystallization and optimization of cell viability after cryopreservation," Glycobiology, vol. 22, No. 1, pp. 123-133, 2012.

Bakhach et al., "The cryopreservation of composite tissues," Organogenesis, vol. 5, No. 3, 119-126, 2009.

Ishiguro et al., "Influence of fish antifreeze proteins on the freezing of cell suspensions with cryoprotectant penetrating cells," Int J. Heat Mass Transfer, 41(13), 1998.

Martinelli et al., "Effect of trehalose on cryopreservation of pure peripheral blood stem cells," Biomedical Reports, vol. 6, 314-318, 2017.

Uebel, CO, "The Punctiform Technique," pp. 641-650 in Hair Transplantation, Walter P. Unger and Ronale Shapiro (eds.), 4th ed., 2004.

Ohyama et al., "Gene Delivery to the Hair Follicle," JID Symposium Proceedings, vol. 8, No. 2, 204-206, Oct. 2003.

\* cited by examiner

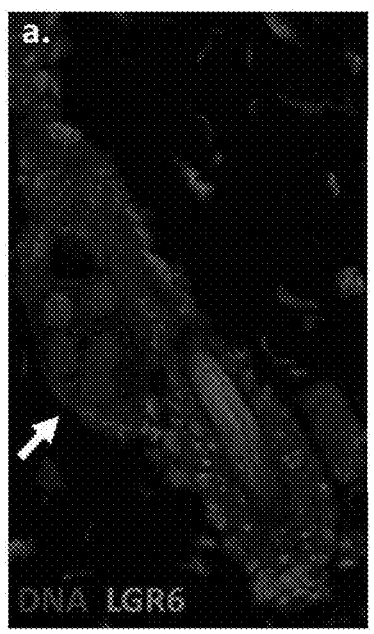
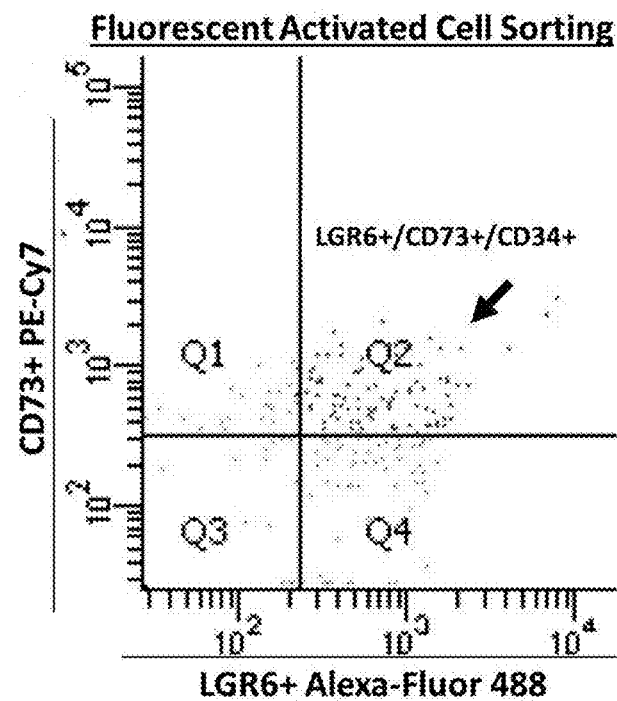
FIG. 1A  FIG. 1B
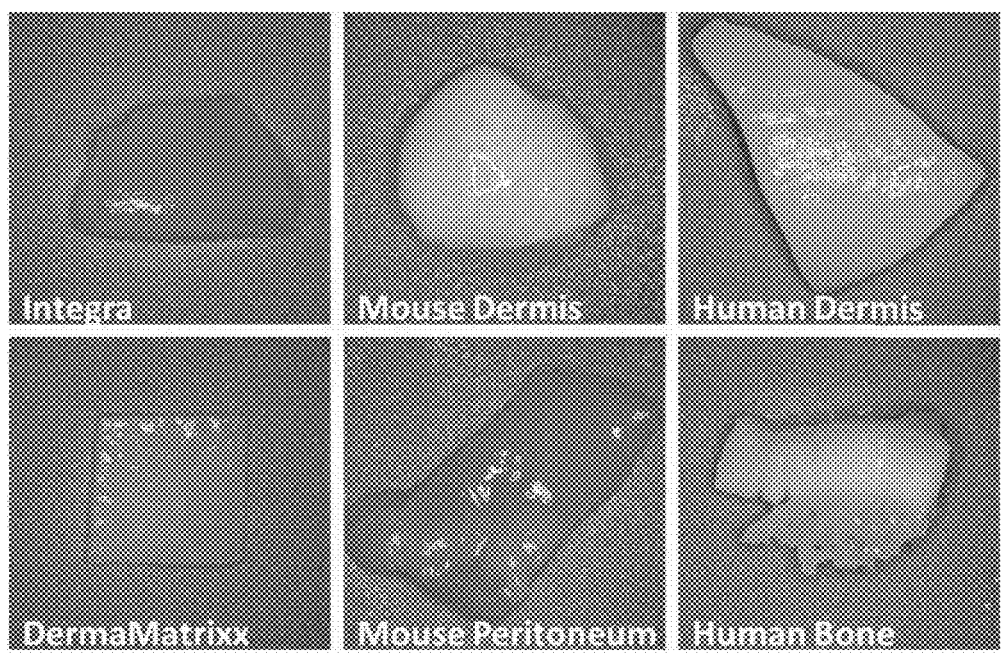
FIG. 1C

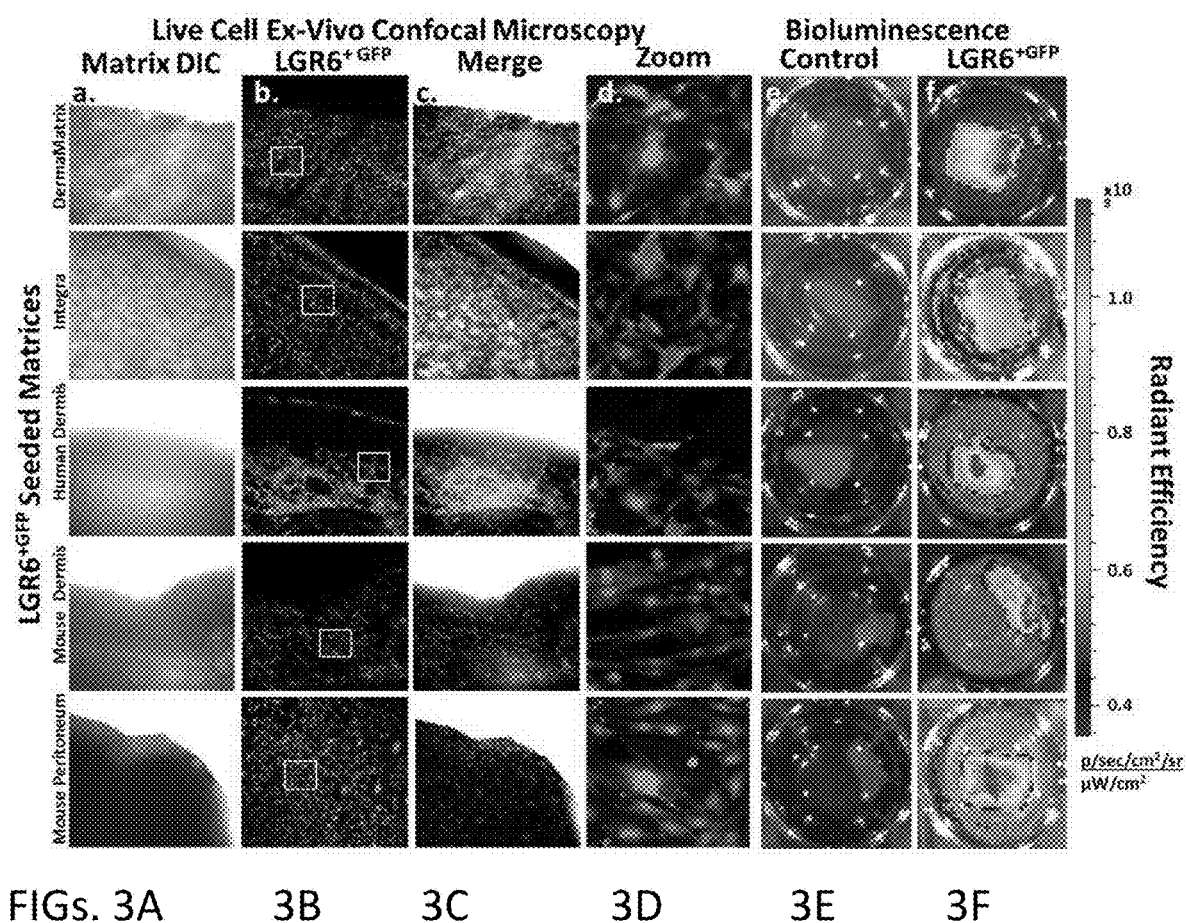
FIGs. 3A    3B    3C    3D    3E    3F

FIGs. 5A  5B  5C
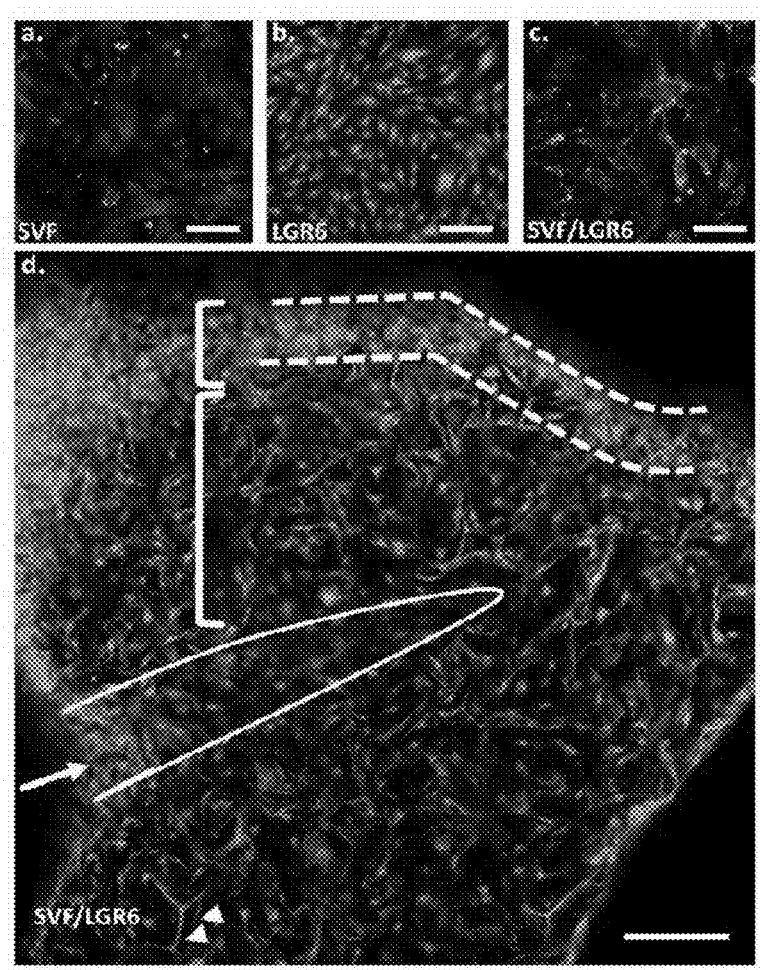
Fig. 5D
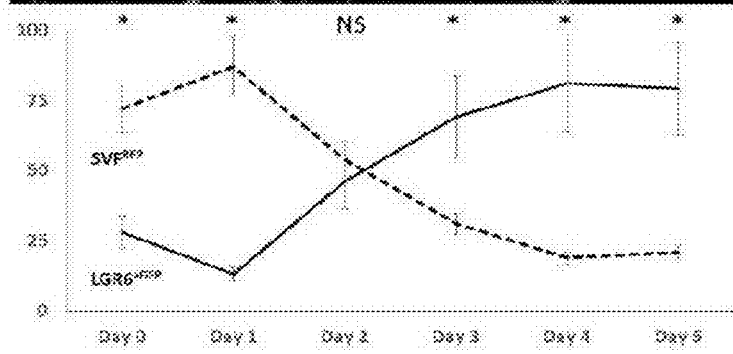
FIG. 5E

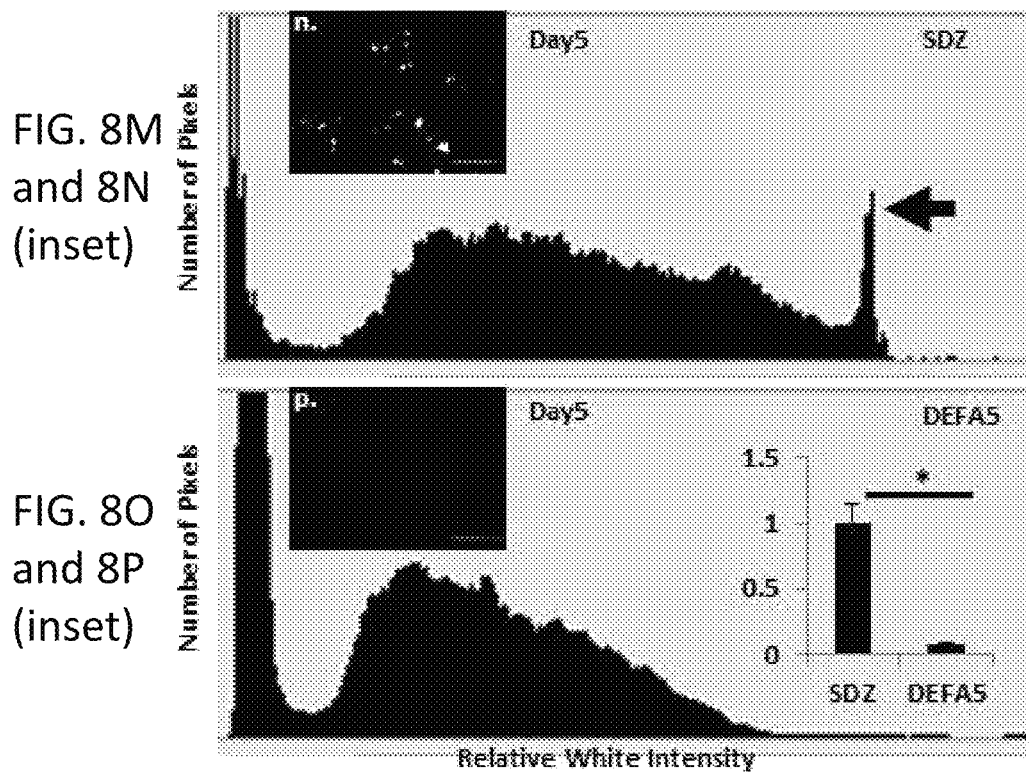
FIG. 8M and 8N (inset)
FIG. 8O and 8P (inset)
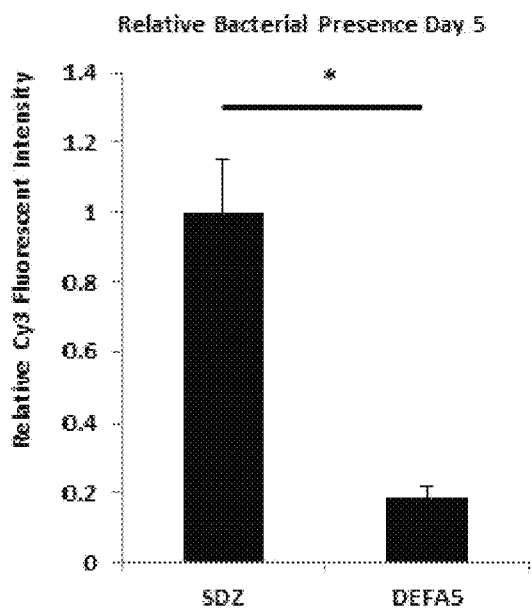
FIG. 8Q

10J a. DAPI DNA
b. FITC LGR5
c. TRITC LGR6
d. MERGE DEFA5 peptide Day 5
e. DAPI DNA
f. FITC LGR5
g. TRITC LGR6
h. MERGE Control SDZ Day 5

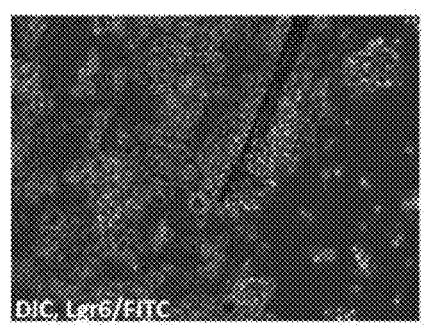
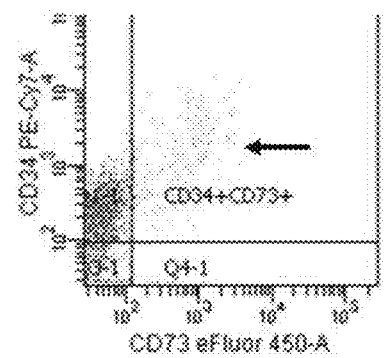
FIG. 12A        FIG. 12B
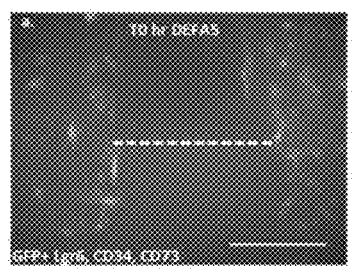
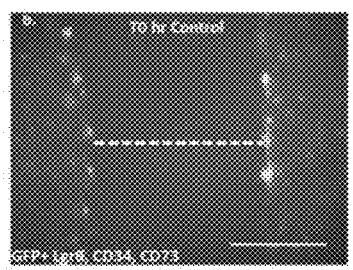
FIG. 12C        FIG. 12D
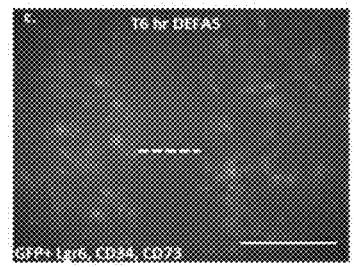
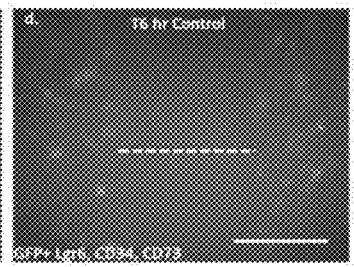
FIG. 12E        FIG. 12F
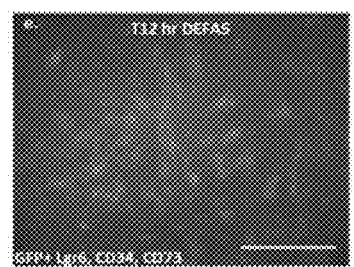
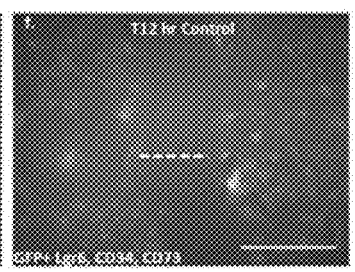
FIG. 12G        FIG. 12H
FIG. 12I
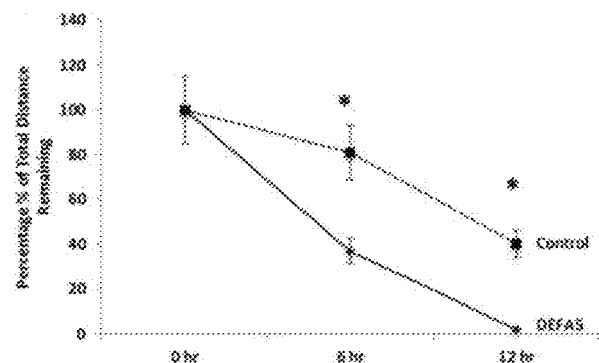

FIG. 13A      FIG. 13B
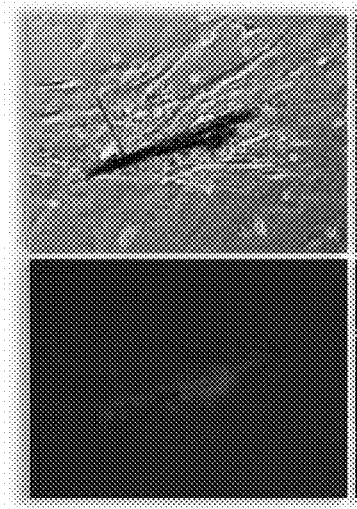
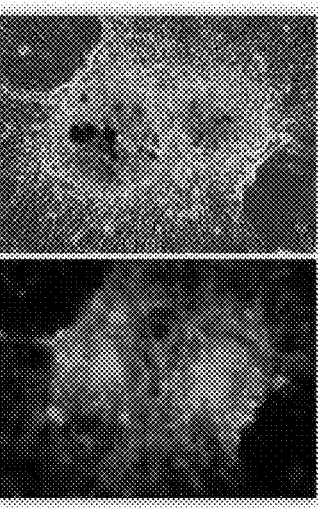
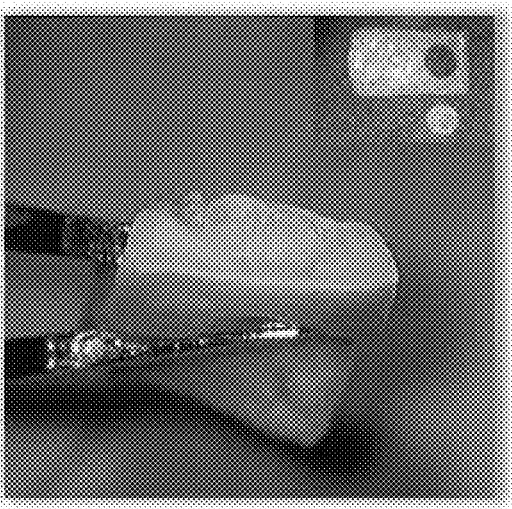
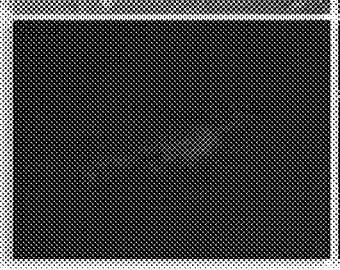
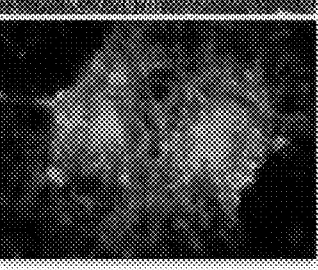
FIG. 13C      FIG. 13D                FIG. 13E

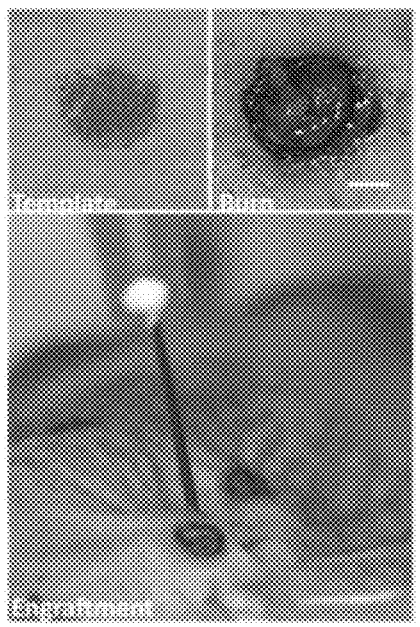
FIG. 15A
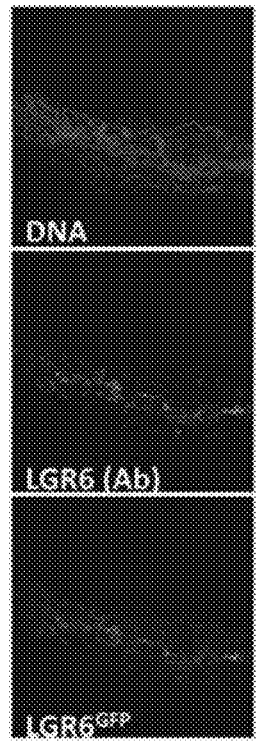
FIG. 15B
FIG. 15C
FIG. 15D
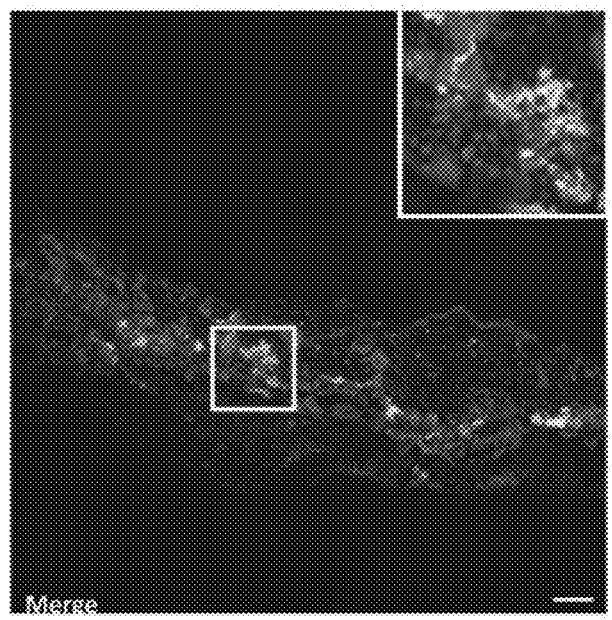
FIG. 15E

METHODS RELATED TO MINIMALLY POLARIZED FUNCTIONAL UNITS

PRIORITY CLAIM

This application claims priority of U.S. Provisional Application Ser. No. 62/086,526 filed Dec. 2, 2014

FIELD OF INVENTION

The present invention relates to constructs of micro-aggregate multicellular grafts containing Leucine-rich repeat-containing G-protein coupled Receptor (LGR) expressing cells for wound therapy applications, tissue engineering, cell therapy applications, regenerative medicine applications, medical/therapeutic applications, tissue healing applications, immune therapy applications, and tissue transplant therapy applications. More particularly, the invention provides a deliverable micro-aggregate multi-cellular LGR construct on a delivery vector/substrate/support/scaffold for direct application.

BACKGROUND

Over the years, clinicians and researchers have searched for antimicrobial agents that not only reduce microorganism wound burden but also possess less cytotoxic side effects. From burns to both acute and chronic wounds, there is the potential for manipulation of naturally-occurring, self-derived antimicrobial peptides, in that these agents typically function through membrane permeabilization, a mechanism less likely to lead to microbial resistance. With the continued risk of infections in wounds and the advancing epidemic of bacterial resistance to current antibiotic therapies, there is a genuine need for the development of a new class of topical antimicrobial agents for use in cutaneous burns and wounds.

There are essentially four phases of wound healing that have been described over the past century: (1) hemostasis, (2) inflammatory, (3) proliferative, and (4) remodeling. These sequential phases were first defined by the types of cells that had migrated into the wound and then later by the type of cytokines and growth factors expressed within the tissues.

With the recent progress in mesenchymal and adipose-derived stem cell isolation and transplantation, researchers have begun to study how these cells improve healing and alter expression within each stage, particularly throughout the later inflammatory to remodeling phases. Much like the mesenchymal and adipose-derived stem cells of the deeper compartment, the epithelial stem cell develops from the primordial ectoderm, which later develops the more superficial epithelial compartment and, thus, also has a potential role in cutaneous wound healing. At this time, there is limited research on how transplantation and application of isolated LGR4, LGR5 and LGR6 expressing epithelial stem cells alter wound healing gene expression.

It is known that LGR4, LGR5 and LGR6 expressing epithelial stem cell populations are often destroyed following severe full-thickness damage to the skin, leaving tissues incapable of producing a viable and self-sustaining epithelial compartment. Despite a combination of granulatory and fibrotic efforts driven by localized inflammation and subsequent chemotaxis of a spectrum of cellular entities, without the epithelial stem cell focal niche, remaining tissues are left without the regenerative potential to form a functional epithelium, hair follicle, sweat gland, or the like.

Complex full thickness injuries to human and mammalian tissues and/or complex injuries involving multiple tissue elements (skin, muscle, fat, blood vessels, nerves and bone) are difficult in nature to heal. Such injuries and subsequent resulting wounds are also difficult to treat through current wound care methods, surgical interventions with current approved technologies utilizing cells, tissues, devices, biologics, drugs and/or growth factors. A common reason for such difficulty is that the tissues remaining in or around a wounded or injured tissue bed are typically devoid of inter-dependent, necessary components: 1) cellular progenitor and/or stem cell populations; 2) extracellular matrix/scaffolding elements and substrates; and 3) a combination of interactions between and among cellular entities and substrates. Such deficiency in the cellular niche, ECM (extracellular matrix) scaffolding and related interactive interfaces subsequently results in failure to re-generate or generate the essential multi-dimensional architecture required for cellular migration, differentiation, and tissue polarization. Without these cell-to-cell and cell-to-matrix interactions, remaining cellular entities within the wound bed, no matter their proliferative or lineage potential, are forced to provide primarily a barrier utility rather than develop a more complex, multi-tissue construct capable of recognizable "function." Consequently, the wound—whether involving skin, muscle, fat, tendon, bone—becomes subsequently scarred, disorganized and dysfunctional.

Current applications in field of tissue engineering of cultured skin, cartilage, bone, muscle, blood vessels, nerves, lymphatics and related substitutes are largely based on a three part strategy: 1) acquiring a tissue source and harvesting cell suspension from such tissue; 2) applying these cells to a matrix or scaffold; and 3) grafting the construct onto or into a target site of a human or animal. However, in the absence of the above-identified inter-dependent, necessary components, tissue engineering applications, cell therapy applications, regenerative medicine applications, tissue healing applications and tissue transplant therapy applications do not possess the natural cellular micro-aggregate architecture needed to competently assemble functional polarized tissues. Thus, due to the lack of proper inter-dependency, progenitor cell mass and proper scaffolding prevent such constructs to be useful in therapeutic applications such as multi-compartment tissue regeneration and/or bone and muscle reconstruction.

Consequently, in part due to the foregoing, substantial efforts and resources have been directed by both industry and academics to developing synthetic tissue substitutes, autograft constructs, as well as patient-derived epidermal expansion autografts (i.e. EPICEL® from Vericel Corporation of Cambridge Mass.). These products, although beneficial, are often expensive and do not provide the patient with a true multi-compartment tissue construct. For example, cultured epithelial autograft (CEA) remains unable to restore both epithelial and dermal compartments seen in native skin. But in view of the absence of interdependent functioning compartments, the cultured cells are left without an expanding localized stem cell population and the evolving tissue polarization needed to develop integument—epidermis, dermis, glands and hair—which truly defines skin. This failure, in turn, leads to monolayer fragility, epithelial instability, barrier breakdown, and scar.

Alternatively, the more robust acellular matrices such as ALLODERM® from LifeCell Corporation, INTEGRA® from Integra LifeSciences Corporation and DERMAMATRIX® a product from Musculoskeletal Transplant Foundation, although excellent reconstructive options, lack those properly placed lineage specific stem cell populations which are necessary to develop functional native tissues.

The inventor herein has already written about the relatively recent recognition of LGR5 and LGR6 as markers of both intestinal and epidermal stem cells in mammals. In Stimulation of the Follicular Bulge LGR5+ and LGR6+ Stem Cells with the Gut-Derived Human Alpha Defensin 5 Results in Decreased Bacterial Presence, Enhanced Wound Healing, and Hair Growth from Tissues Devoid of Adnexal Structures, Plast. Reconstr. Surg. 132: 1159, 2013, Leucine-rich repeat-containing G-protein—coupled receptor (LGR) is a seven-pass transmembrane protein receptor with significant sequence and structural homology to the follicle-stimulating hormone, thyroid-stimulating hormone, and luteinizing hormone receptor families.

In that study, it was recognized that human alpha defensin 5 peptide significantly enhanced wound healing and reduced basal bacterial load compared with human beta defensin 1 and sulfadiazine. Human alpha defensin 5 was the only therapy to induce LGR stem cell migration into the wound bed. In addition, gene heat mapping showed significant mRNA up-regulation of key wound healing and Wnt pathway transcripts such as Wnt1 and Wisp1. So it was concluded that human alpha defensin 5 could be used for enhanced wound healing due to the observed increase of LGR stem cell migration into wound beds and associated bacterial reduction and hair production through the augmentation of key Wnt and wound healing transcripts. In short, this and other work led to the recognition of the potential for using LGR4+, LGR5+ and LGR6+ expressing epithelial stem cells in direct biomedical engineering soft tissue constructs.

SUMMARY OF INVENTION

The invention provides in a first embodiment a minimally polarized micro-aggregate multi-cellular composition including isolated living LGR expressing cells and a multi-dimensional support selected from the group consisting of scaffolding, collagen, matrix, particle, and fiber.

The invention provides in a further embodiment to the previous embodiment a minimally polarized micro-aggregate multi-cellular composition including isolated living LGR expressing cells and a multi-dimensional support selected from the group consisting of scaffolding, collagen, matrix, particle, and fiber where the LGR expressing cells are supplemented with growth factors and where the LGR expressing cells are selected from the group consisting of LGR4, LGR5 and LGR6.

The invention provides in a further embodiment to any of the previous embodiments a minimally polarized micro-aggregate multi-cellular composition including isolated living LGR expressing cells and a multi-dimensional support selected from the group consisting of scaffolding, collagen, matrix, particle, and fiber where the LGR expressing cells are supplemented with migratory/recruiting analytes and the LGR expressing cells being selected from the group consisting of LGR4, LGR5 and LGR6.

The invention provides in a further embodiment to any of the previous embodiments a minimally polarized micro-aggregate multi-cellular composition including isolated living LGR expressing cells and a multi-dimensional support selected from the group consisting of scaffolding, collagen, matrix, particle, and fiber where the LGR expressing cells are supplemented with LGR specific binding elements selected from the group consisting of ligand families, R-spondin, EDGF, PDGF, Wnt, VEGF, and antimicrobial peptides and where the LGR expressing cells are selected from the group consisting of LGR4, LGR5 and LGR6.

The invention provides in a further embodiment to any of the previous embodiments a minimally polarized micro-aggregate multi-cellular composition including isolated living LGR expressing cells and a multi-dimensional support selected from the group consisting of scaffolding, collagen, matrix, particle, and fiber where the composition is used as a therapeutic construct for a select target consisting of a tissue region, wound, void, defect tissue, or blood for alteration of either surrounding adjacent tissues.

The invention provides in a further embodiment to any of the previous embodiments a minimally polarized micro-aggregate multi-cellular composition characterized by a isolated living LGR expressing cells transplanted to damaged tissue to accelerate healing thereof.

The invention provides in a further embodiment to any of the previous embodiments a minimally polarized micro-aggregate multi-cellular composition for tissue system repair or restoration throughout the body comprising a support scaffolding with isolated LGR containing cells secured thererto.

The invention provides in a further embodiment to any of the previous embodiments a tissue graft for application to ectodermal, mesodermal or endodermal-derived tissues systems throughout a mammalian body Another embodiment of the invention is characterized by a method for obtaining a minimally polarized micro-aggregate multi-cellular composition characterized by the steps of growing and isolating living LGR expressing cells for transplantation to a select mammalian target tissue.

The invention provides in a further embodiment to the foregoing method a method for obtaining a minimally polarized micro-aggregate multi-cellular composition characterized by the steps of growing and isolating living LGR expressing cells for transplantation to a select mammalian target tissue further characterized by the step of affixing the isolated living LGR expressing cells to a multi-dimensional support selected from the group consisting of scaffolding, collagen, matrix, particle, and fiber.

The invention is characterized in still another embodiment by a method for obtaining a minimally polarized micro-aggregate multi-cellular composition characterized by the steps of growing and isolating living LGR expressing cells for transplantation to a select mammalian target tissue further characterized by the step of selecting the LGR expressing cells from the group consisting of LGR4, LGR5 and LGR6.

The invention provides in a further embodiment to any of the previous method embodiments the step of applying the minimally polarized micro-aggregate multi-cellular to one of the group consisting of epithelial systems, glands, hair, nerves, bone, muscle, fat, tendons, blood vessels, fascia, ocular tissues and peptide secreting cellular elements employing delivery by a technique selected from the group consisting of application, transplantation, implantation, directed seeding, directed migration, directed tracking, in setting, laminating and/or injection of the cellular element generating, regenerating, enhancing and healing.

The invention provides in a further embodiment to any of the previous method embodiments a method for obtaining a minimally polarized micro-aggregate multi-cellular composition characterized by the steps of growing and isolating living LGR expressing cells for transplantation to a select mammalian target tissue further characterized by the step of applying the minimally polarized micro-aggregate multi-cellular composition directly to a tissue in vivo for tissue restoration.

The invention provides in a further embodiment to any of the previous method embodiments a method for obtaining a minimally polarized micro-aggregate multi-cellular composition characterized by the steps of growing and isolating living LGR expressing cells for transplantation to a select mammalian target tissue further characterized by the step indirectly applying the minimally polarized micro-aggregate multi-cellular composition via the blood stream for tissue restoration in a body.

The invention is characterized in yet another embodiment by a method for producing a minimally polarized micro-aggregate multi-cellular composition characterized by the steps of:

a) obtaining a tissue specimen;
b) extracting minimally polarized functional units containing LGR expressing cells from the specimen;
c) processing of hypodermis and subdermal fat cellular components from an appropriate source;
d) adding the processed hypodermis and subdermal fat components to the extracted minimally polarized functional units to create epithelial stem cell singularity units;
e) enriching the epithelial stem cell singularity units;
f) adding the epithelial stem cell singularity units to a construct scaffold; and
g) verifying the maintenance of minimum polarization of the obtained composition.

The invention provides in a further embodiment to any of the previous embodiments a media formulation used in obtaining minimally polarized micro-aggregate multi-cellular compositions using cell sustaining media composition for reducing the viability of micro-organisms during transport and processing of tissues, characterized by: a) a mixture of epithelial cells and keratinocytes; b) at least one agent selected from the group consisting of penicillin, streptomycin, and amphotericin B; and c) fibrinogen.

The invention provides in a further embodiment to the previous embodiment a cell sustaining media composition of for reducing the viability of micro-organisms during transport and processing of tissues, characterized by: a) a mixture of epithelial cells and keratinocytes; b) at least one agent selected from the group consisting of penicillin, streptomycin, and amphotericin B; and c) fibrinogen, where the fibrinogen is human and where the agent includes both an antibiotic and an antimycotic for stabilizing human tissues.

In the context of a first aspect of the invention, it is characterized by LGR expressing cells being applied to scaffolding matrix, and/or fiber to thereby establish micro-aggregate multi-cellular grafts for tissue engineering applications, cell therapy applications, regenerative medicine applications, medical/therapeutic applications the grafts being directly applied to tissue or blood for improvement and or alteration of epithelial systems throughout the body.

A second aspect of the invention is characterized by LGR expressing cells being applied to scaffolding, matrix, and/or fiber or without additional enhancing factors or analytes before or after either being applied to tissue or blood for improvement and or alteration of in vivo epithelial systems.

A further aspect of the invention is characterized by LGR expressing cells altered by enhancing factors or analytes, being applied as targets within the body, tissue or blood for improvement and or alteration of epithelial systems through local or distant migration throughout the body and/or to restore gland and hair growth.

A fourth aspect of the invention is characterized by transplanting LGR expressing cells from tissue, blood or culture for alteration of surrounding adjacent tissues or distant tissues such as but not inclusive of LGR expressing cells applied to scaffolding, matrix, and fiber before or after either being applied to tissue or blood for improvement and or alteration of ectodermal, mesodermal or endodermal-derived tissues systems throughout the body.

A fifth aspect of the invention is characterized by directly applying LGR expressing cells to a delivery substrate vehicle selected from a group consisting of scaffolding, matrix, and fiber with/or without additional enhancing factors or analytes before or after either being applied to tissue or blood for improvement and or alteration of ectodermal, mesodermal or endodermal-derived tissues systems throughout the body.

Still another aspect of the invention is characterized by combining LGR expressing cells altered by enhancing factors or analytes, with a delivery support substrate as targets within the body, tissue or blood for improvement and or alteration of ectodermal, mesodermal or endodermal-derived tissues systems throughout the body through local or distant migration throughout the body.

A further aspect of the invention is characterized by adhering LGR expressing cells to a support substrate for the delivery, application, transplantation, implantation, directed seeding, directed migration, directed tracking, in setting, laminating and/or injection of the cellular element generating, regenerating, enhancing and/or healing epithelial systems, glands, hair, nerves, bone, muscle, fat, tendons, blood vessels, fascia, ocular tissues and peptide secreting cellular elements.

A final stated aspect of the invention is to generate LGR expressing stem cells as micro-aggregate multi-cellular functional units exhibiting minimal polarization for transplantation and direct application to a target within a mammalian body, tissue or blood to enhance and accelerate tissue generating, regenerating, enhancing and/or healing.

In most general terms, the invention herein contemplates the transplanting and/or delivery of isolated LGR expressing cells (Leucine-rich repeat-containing G-protein coupled receptor) for the generation, regeneration, recruitment or enhancement of an epithelial system, hair, gland bone. The invention also contemplates application to both local/proximate and distant/remote tissue in clinical medicine, bioengineering and/or research constructs using a delivery vehicle in the form of scaffolding, matrix or fiber with or without the supplementation of growth factors migratory/recruiting analytes or LGR specific binding elements such as but not limited to ligand families: R-spondin, EDGF, PDGF, Wnt, VEGF, antimicrobial peptides.

Use of the LGR epithelial stem cells, particularly in conjunction with a formed scaffolding substrate, provides full thickness wounds and or voids in epithelial systems with a stem cell enriched tissue substitute. Moreover, the addition of this minimally polarized functional cell unit (MPFU) to an epithelial system enhances/improves the status of that epithelium which includes the growth, generation or regeneration of hair, glands, secreted anti-microbial peptides, growth factors and analytes generally required to maintain and promote the health and viability of the epithelium and local surrounding tissues elements.

Recognizing that LGR4+, LGR5+ and LGR6+ stem cell and progenitor cell proliferation kinetics remain high, especially when in contact with substrate scaffolding, complete epithelial turnover rates are typically less than 12 days (1 cm inter-population distance spacing). This capacity to regenerate a sufficient tissue bi-layer and subsequent barrier function suggests a role for these cells as a type of evolving biologic dressing for complex full thickness and multi-tissue wounds.

Beyond a capacity to regenerate skin, muscle and bone quickly, the progenitors of the LGR4, LGR5 and LGR6 stem cells also have the ability to generate native anti-microbial peptides that not only reduce the basal level of microorganisms within the wound bed but also augment progenitor cells amplification and differentiation, leading to a reduction in wound and peri-wound infections, faster wound closure, and hair follicle development.

The invention herein describes the translational applicability of an LGR expressing epithelial stem cell-seeded scaffold in providing an immediate, deliverable and viable tissue barrier that is capable of maintaining a stem cell colony focus with concomitant competent progeny. From these stem cell foci, progeny can undergo migratory proliferative-differentiation in order to stimulate epithelial tissue elements, healing and graft integration. It has been found that the LGR epithelial stem cells can be applied alone, with scaffolding, soluble growth factors and/or additional cell lineage which promote the polarization of the scaffold bound populations as well as intrinsic tissue architecture required in epithelial healing and cellular regenerative efforts.

Broadly defined, the protocol of the invention involves: a) harvesting living human/mammalian tissue; b) processing the tissue element to generate a micro-aggregate multicellular functional units which contain LGR expressing cells; c) applying the LGR expressing cell micro-aggregate multi-cellular functional units to a delivery vehicle substrate selected from the group consisting of scaffolding, matrix, particle, cell(s) and fiber to create a construct; d) optionally including selected additional enhancing factors; and e) applying the construct to tissues for generating, regenerating, enhancing and/or healing tissue systems including those related to ectodermal, mesodermal and/or endodermal origin tissues including but not limited to skin, glands, hair, nerves, bone, muscle, fat, tendons, blood vessels, fascia, ocular tissues, bone marrow, lung, heart, nails, gastrointestinal tissues, oral tissues, teeth, taste buds, urogenital tissues, renal tissues, reproductive tissues, lymphatic tissues, immune system tissues/elements and such related appendages and protein cellular elements.

This invention contemplates the direct delivery of supported LGR expressing epithelial stem cells by application, transplantation, implantation, directed seeding, directed migration, directed tracking, in setting, laminating and/or injection of the cellular element to alter mammalian tissue(s) in therapeutics, devices, biologics, drugs and bio-engineering.

Definitions

In this detailed description, references to "one embodiment", "an embodiment", or "in embodiments" mean that the feature being referred to is included in at least one embodiment of the invention. Moreover, separate references to "one embodiment", "an embodiment", or "embodiments" do not necessarily refer to the same embodiment; however, neither are such embodiments mutually exclusive, unless so stated, and except as will be readily apparent to those skilled in the art. Thus, the invention can include any variety of combinations and/or integrations of the embodiments described herein. The terminology used herein is for the purpose of describing particular embodiments only and is not intended to be limiting of the invention.

As used herein, the singular forms, "a", "an" and "the" are intended to include the plural forms as well, unless the context clearly indicates otherwise. It will be further understood that the root terms "include" and/or "have", when used in this specification, specify the presence of stated features, steps, operations, elements, and/or components, but do not preclude the presence or addition of at least one other feature, step, operation, element, component, and/or groups thereof.

As used herein Bone means the hard connective tissue consisting of cells embedded in a matrix of mineralized ground substance and collagen fibers. The fibers are impregnated with inorganic components, including crystals of calcium phosphate, such that using X-ray defraction, they are seen to be organized in a hydroxyapatite pattern (calcium phosphate is 85% by weight) as well as calcium carbonate (10%), and magnesium; by weight, bone is composed of 65-75% inorganic and 25-35% organic material; a portion of osseous tissue of definite shape and size, forming a part of the animal skeleton; in humans there are approximately 200 distinct bones in the skeleton, not including the auditory ossicles of the tympanic cavity or the sesamoid bones other than the two patellae. A bone is enveloped by a fibrous membrane, periosteum that covers the bone's entire surface except for the articular cartilage. Beneath the periosteum is a dense layer, compact bone, and beneath that a cancellous layer, spongy bone. The core of a long bone is filled with marrow.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus.

As used herein Epithelium means the cellular layer covering all free surfaces, cutaneous, mucous, and serous, including the glands and other structures derived therefrom.

As used herein GMP means good manufacturing practices.

As used herein Integument means the enveloping membrane of the body; includes, in addition to the epidermis and dermis, all the derivatives of the epidermis, hairs, nails, sudoriferous and sebaceous glands, and mammary glands, as well as the subcutaneous tissue.

As used herein LGR4 means Leucine-Rich Repeat Containing G Protein-Coupled Receptor 4, G protein-coupled receptors (GPCRs) that play key roles in a variety of physiologic functions. Members of the leucine-rich GPCR (LGR) family, such as GPR48, have multiple N-terminal leucine-rich repeats (LRRs) and a 7-transmembrane domain. LGR4 (Leucine-Rich Repeat Containing G Protein-Coupled Receptor 4) is a Protein Coding gene. Diseases associated with LGR4 include bone mineral density, low. Among its related pathways are Wnt signaling pathway (KEGG). GO annotations related to this gene include G-protein coupled receptor activity and transmembrane signaling receptor activity. An important paralog of this gene is LGR6. Receptor for R-spondins that potentiates the canonical Wnt signaling pathway and is involved in the formation of various organs. Upon binding to R-spondins (RSPO1, RSPO2, RSPO3 or RSPO4), associates with phosphorylated LRP6 and frizzled receptors that are activated by extracellular Wnt receptors, triggering the canonical Wnt signaling pathway to increase expression of target genes.

In contrast to classical G-protein coupled receptors, LGR4 does not activate heterotrimeric G-proteins to transduce the signal. Its function as activator of the Wnt signaling pathway is required for the development of various organs, including liver, kidney, intestine, bone, reproductive tract and eye. LGR4 may also act as a receptor for norrin (NDP) and is required during spermatogenesis to activate the Wnt signaling pathway in peritubular myoid cells. Likewise, LGR4 is required for the maintenance of intestinal stem cells and Paneth cell differentiation in postnatal intestinal crypts. LGR4 also acts as a regulator of bone formation and remodeling in addition to being involved in kidney development; required for maintaining the ureteric bud in an undifferentiated state. LGR4 is involved in the development of the anterior segment of the eye, required during erythropoiesis and also acts as a negative regulator of innate immunity by inhibiting TLR2/TLR4 associated pattern recognition and pro-inflammatory cytokine production. LGR plays an important role in regulating the circadian rhythms of plasma lipids, partially through regulating the rhythmic expression of MTTP (By similarity). Commonly known aliases for LGR4 include: GPR48; G Protein-Coupled Receptor 48; BNMD17; Leucine-Rich Repeat-Containing G Protein-Coupled Receptor 4; Leucine-Rich Repeat-Containing G Protein Coupled Receptor 4; and G-Protein Coupled Receptor 48. External Database Identifiers for LGR4 include: HGNC: 13299 Entrez Gene: 55366 Ensembl: ENSG00000205213 OMIM: 606666 and UniProtKB: Q9BXB.

As used herein LGR5 means Leucine-Rich Repeat Containing G Protein-Coupled Receptor 5, a Protein Coding gene. Among its related pathways are Wnt signaling pathway (KEGG). GO annotations related to this gene include G-protein coupled receptor activity and transmembrane signaling receptor activity. An important paralog of this gene is LGR6. The LGR5 Receptor is for R-spondins that potentiates the canonical Wnt signaling pathway and acts as a stem cell marker of the intestinal epithelium and the hair follicle. Upon binding to R-spondins (RSPO1, RSPO2, RSPO3 or RSPO4), associates with phosphorylated LRP6 and frizzled receptors that are activated by extracellular Wnt receptors, triggering the canonical Wnt signaling pathway to increase expression of target genes. In contrast to classical G-protein coupled receptors, LGR5 does not activate heterotrimeric G-proteins to transduce the signal. Involved in the development and/or maintenance of the adult intestinal stem cells during postembryonic development. Commonly known aliases for LGR5 include: G-Protein Coupled Receptor HG38; G-Protein Coupled Receptor 49; G-Protein Coupled Receptor 67; GPR67; GPR49 and Leucine-Rich Repeat-Containing G-Protein Coupled Receptor 5. External Database Identifiers for LGR5 include HGNC: 4504 Entrez Gene: 8549 Ensembl: ENSG00000139292 OMIM: 606667 and UniProtKB: O75473.

As used herein LGR6 means Leucine-Rich Repeat Containing G Protein-Coupled Receptor 6 which is a Protein Coding gene a gene that encodes a member of the leucine-rich repeat-containing subgroup of the G protein-coupled 7-transmembrane protein superfamily. The encoded protein is a glycoprotein hormone receptor with a large N-terminal extracellular domain that contains leucine-rich repeats important for the formation of a horseshoe-shaped interaction motif for ligand binding. Alternative splicing of this gene results in multiple transcript variants. Diseases associated with LGR6 include myxedema and ovarian cystadenoma. Among its related pathways are Wnt signaling pathway (KEGG) and GPCRs, Other annotations related to this gene include G-protein coupled receptor activity and transmembrane signaling receptor activity. An important paralog of this gene is TSHR. Receptor for R-spondins that potentiates the canonical Wnt signaling pathway and acts as a marker of multipotent stem cells in the epidermis. Upon binding to R-spondins (RSPO1, RSPO2, RSPO3 or RSPO4), associates with phosphorylated LRP6 and frizzled receptors that are activated by extracellular Wnt receptors, triggering the canonical Wnt signaling pathway to increase expression of target genes. In contrast to classical G-protein coupled receptors, LGR6 does not activate heterotrimeric G-proteins to transduce the signal and can act as a tumor suppressor. Common aliases for LGR6 include: Gonadotropin Receptor; VTS20631 and GPCR. External Database Identifiers for LGR6 include HGNC: 19719 Entrez Gene: 59352 Ensembl: ENSG00000133067 OMIM: 606653 and UniProtKB: Q9HBX8.

As used herein Mesenchyme means an aggregation of mesenchymal cells. Primordial embryonic connective tissue consisting of mesenchymal cells, usually stellate in form, supported in inter-laminar jelly.

As used herein Muscle means the primary tissue, consisting predominantly of highly specialized contractile cells, which may be classified as skeletal muscle, cardiac muscle, or smooth muscle; microscopically, the latter is lacking in transverse striations characteristic of the other two types; one of the contractile organs of the body by which movements of the various organs and parts are effected; typical muscle is a mass of musculus fibers (venter or belly), attached at each extremity, by means of a tendon, to a bone or other structure; the more proximal or more fixed attachment is called the origin (q.v.), the more distal or more movable attachment is the insertion (q.v.); the narrowing part of the belly that is attached to the tendon of origin is called the caput or head.

As used herein Neural is intended to include any structure composed of nerve cells or their processes, or that on further development will evolve into nerve cells. Referring to the dorsal side of the vertebral bodies or their precursors, where the spinal cord is located, as opposed to hemal.

As used herein, and unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

The meaning of Particle herein connotes the largest domain of which is ten micron or less and includes, but is not limited to, nanoparticles, an association of macromolecules, a micelle, a cell ghost, a dendrimer, and the like that can serve as a suitable anchor for a cell micro-aggregate.

As used herein Polarity means the tendency of a cell, tissue(s) and/or organism to develop differentially along an axis.

As used herein Pulse Rescue Media (PRM) is a formulation of a cell sustaining media mixture including Keratinocyte-SFM (1×), an antibiotic-antimycotic selected from the group consisting of penicillin, streptomycin, and amphotericin B, and fibrinogen where the Keratinocyte-SFM is composed of a mixture of epithelial cells and keratinocytes. The reagents are utilized in order to stabilize the primary tissues and reduce the viability of micro-organisms during transport and processing.

As used herein Skin means the membranous protective covering of the body, consisting of the epidermis and dermis (corium).

As used herein Stem cell means any precursor cell; a cell with daughter cells that may differentiate into other cell types; a cell capable of maintaining its own number while exporting progeny to one or more cell lineages.

As used herein "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

As used herein Tissue means a collection of similar cells and the intercellular substances surrounding them. There are four basic kinds of tissue in the body: epithelium; connective tissues including adipose tissue, blood, bone, and cartilage; muscle tissue; and nerve tissue. The rind, capsule, or covering of any body or part.

In the following description, reference is made to the accompanying drawings which are provided for illustration purposes. The following illustrated embodiment is described in sufficient detail to enable those skilled in the art to practice the invention. It is to be understood that other embodiments may be utilized and that structural changes based on presently known structural and/or functional equivalents may be made without departing from the scope of the invention.

BRIEF DESCRIPTION OF THE DRAWINGS

FIG. 1A depicts an example of location of LGR expressing cells of cutaneous origin.

FIG. 1B is a Fluorescent Activated Cell Sorting graph.

FIG. 1C are photographs of a spectrum of various acellular supports contemplated for use in connection with the invention.

FIG. 3A-3F present various images by different techniques of an array of different LGR6+ epithelial stem cell seeded substrates.

FIGS. 5A-E depict an example of a construct with LGR ESCs and stromal vascular fraction cellular isolate populations showing initial form of polarization accompanied by a graphic comparison.

FIGS. 10A-L illustrate the quantification of wound bed healing kinetics and LGR5 and LGR6 stem cell migration into burn tissue following treatment with topical focal.

FIGS. 12A-I illustrate LGR6 expression of cells of the hair follicle and fluorescent activated cell sorting of co-expressing LGR6+, CD34+ CD73+ GFP labeled cells for culture expansion.

FIGS. 13A-D are photomicrographs by confocal microscopy and bioluminescence of a functional singularity unit (aFSU) at the time initial seeding and 1 day later.

FIG. 13E is a photomicrograph of a collagen scaffold.

FIGS. 15A-E provides an example of LGR expressing cellular foci as it relates to a method of delivery through placement around and/or within wound/injury/tissue void.

FIGS. 16A-D depict an example of LGR containing stem cell focus as it relates to delivery into and around wounds via a deliverable vector and subsequent healing, regeneration of tissues and supporting structures.

DETAILED DESCRIPTION OF THE DRAWINGS

FIGS. 1A-C Example of flow cytometry of cell populations that exist around a hair follicle and scaffolds that such cells readily adhere to when seeded. More specifically, FIG. 1A depicts an example of location of said LGR expressing cells of cutaneous origin. Immunofluorescent confocal microscopy at 40× magnification depicts the follicular bulge (white arrow), LGR6+ (Green), DNA (Blue). FIG. 1B is a fluorescent activated cell sorting graph with gate analysis indicating exemplary cellular markers. FIG. 1C depicts an array of cells types can be used to seed a spectrum of acellular matrices/substrates/scaffolds/materials according to the invention.

Figure 2A:
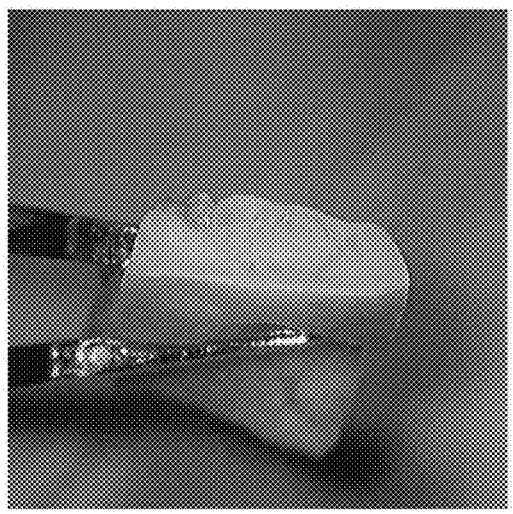
FIG. 2A is photograph of a gross cellular construct/decellularized collagen scaffold usable for seeding.
Figure 2B:
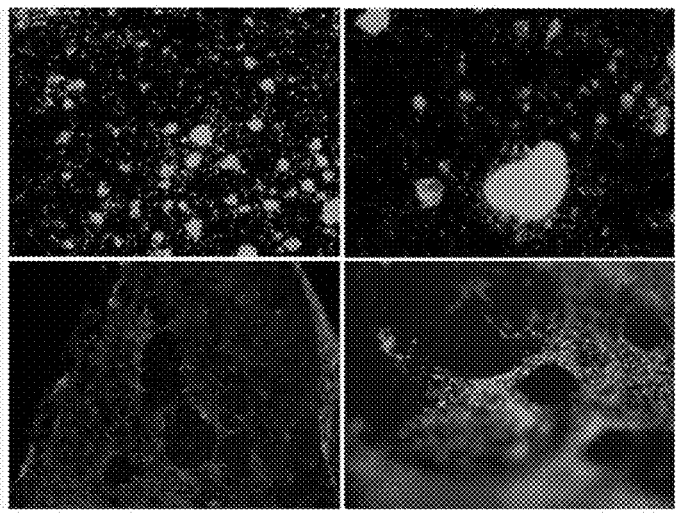
FIG. 2B are immunofluorescent photomicrographs of a collagen construct following seeding with aggregates of partially digested cells.

FIG. 2A is a photographic representation of an example of a gross construct without micro-aggregate multi-cellular functional units containing LGR expressing stem cell foci in accordance with the invention. FIG. 2B depicts the construct following seeding of substrate with aggregates of partially digested cells.

FIG. 3A, in columnar format, is an image series by differential interference contrast (DIC) confocal microscopy of LGR seeded substrates from different sources. FIG. 3B is a corresponding column by immunofluorescent confocal microscopy at 20× magnification of LGR6+ ESC seeded matrices of respective constructs containing LGR expressing cells. The inset white boxes represent focal zoom regions indicated in the column FIG. 3D while FIG. 3C is a column depicting the Digital merge of the respective image of FIG. 3A (DIC) and the immunofluorescent of FIG. 3B indicating matrix contour and boundaries. The columns of FIGS. 3E and 3F respectively represent the bioluminescence measured in radiant efficiency of an acellular matrix control and a corresponding LGR6+ ESC seeded matrix at 72 hours post-seeding.

Figure 4A:
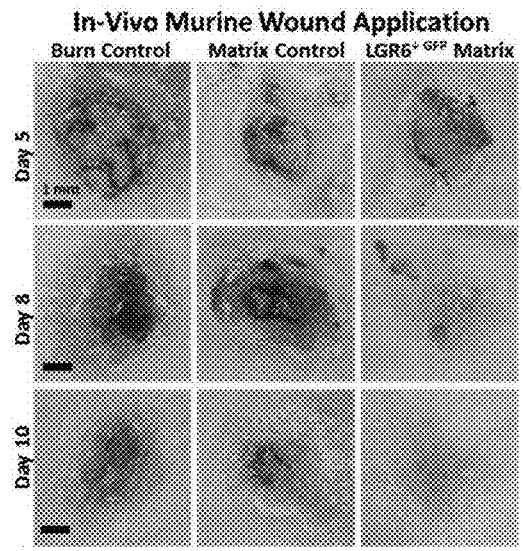
FIG. 4A depicts-a time lapse in vivo healing progression of controls and an example of an LGR seeded matrix.
Figure 4B:
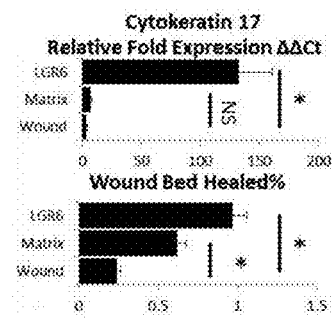
FIG. 4B is a graphical expression of Cytokeratin-17 transcript expression at day ten.

FIG. 4A-E depict examples of said LGR containing construct placed into living mammalian system. Placement of an LGR6+ GFP ESC Seeded Matrix Augments Healing Hair Follicle Growth. FIG. 4A is a 3×3 matrix of photomicrographs of 3 mm full human de-cellularized dermis thickness burn wound beds at days 5, 8 and 10 containing no matrix (burn control), matrix (matrix control) and LGR6+ GFP ESC. FIG. 4B graphically depicts the relative expression of Cytokeratin-17 transcript expression at day 10 of the wound beds depicted in FIG. 4A. The percent wound bed healed was determined using quantification analysis of wound bed healing rates as a percent area function within the ImageJ NCBI application. Wound control contains burn wound bed only. Matrix control contains matrix only and LGR6+ GFP contains ADM seeded with LGR6+ GFP ESCs.

Figure 4C:
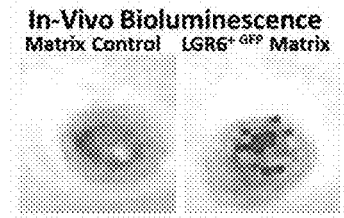
FIGS. 4C-E depict controls and a matrix seeded with LGR ESC by bioluminescent imaging and scanning electron microscopy.
Figure 4D:
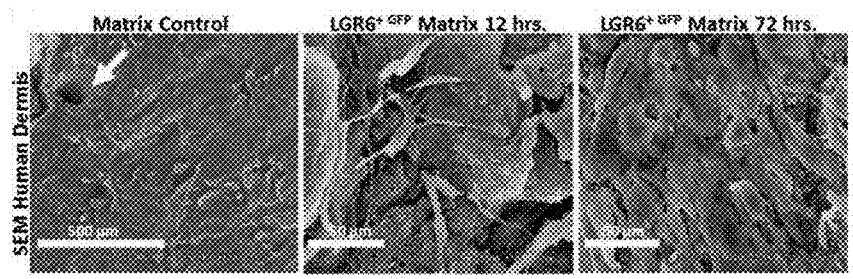
Figure 4E:
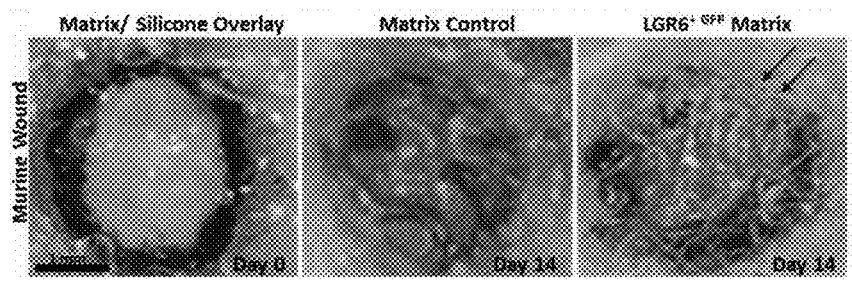

FIG. 4C is a photomicrograph of in vivo bioluminescent imaging in murine full thickness burn wound beds at day 5. FIG. 4D are micrographs of human dermis at 100× of the controls and LGR6+ GFP containing dermis at 12 hours and 72 hours and after seeding with ESCs. The white arrow indicates the presence of a dermal pore FIG. 4E provides images of the controls and the construct of the invention containing human dermis seeded with ESCs with a silicone protective overlay to prevent desiccation. The LGR6+ GFP matrix image includes duplicate small black arrows that indicate nascent hair patches from the full thickness Nu/Nu murine wound bed.

FIGS. 5A-E depict an example of said construct the effect of addition of Stromal vascular fraction (SVF) to LGR6+ ESC Seeded Matrices in promoting tissue polarization and a dual compartment skin-like System. FIG. 5A is confocal 20× imaging of a 5×10$^5$ RFP expressing stromal vascular fraction cellular isolate population 24 hours after being seeded on to a representative Adrenomedullin (ADM) (such as that available from Integra LifeSciences Corporation under the name INTEGRA®). FIG. 5B is a confocal 20× image of a 5×10$^5$ GFP expressing LGR6$^+$ cellular isolate population 24 hours after being seeded on to a representative ADM (INTEGRA®). FIG. 5C depicts confocal 20× imaging of a dual seeded representative ADM (INTEGRA®) with 5×10$^5$ RFP expressing SVF and 5×10$^5$ GFP expressing LGR6$^+$ isolate populations 24 hours after being co-seeded in culture. FIG. 5D is of a co-seeded matrix containing 5×10$^5$ RFP expressing SVF$^{RFP}$ and 5×10$^5$ GFP expressing LGR6$^+$ following 5 days of growth in culture. The dotted parallel lines indicate epithelial LGR6$^{+GFP}$ lineage accumulating at the edge of the ADM substrate. The small bracket and large bracket indicate the relative locations of the two compartments in correlation with LGR6$^{+GFP}$ and SVF$^{RFP}$ abundance. The arrowed "U" shaped solid line indicates a region containing a pre-seeded pore induced by a 32 gauge sterile needle. FIG. 5E is a graphical representation of the proliferation kinetics of a collagen substrate co-seeded with green LGR expressing cells and red SVF expressing cells.

Figure 6A:
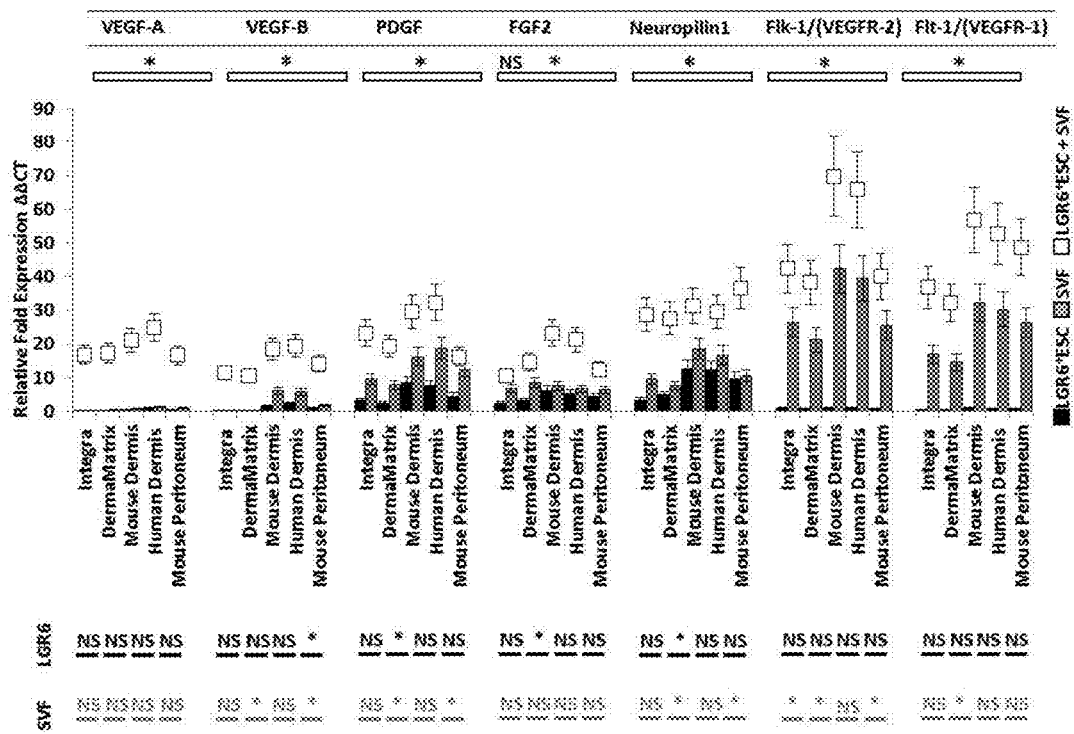
FIGS. 6A-B depict an example of a construct containing LGR cells with and without stromal vascular fraction cellular entities and the relative production of growth factors.
Figure 6B:
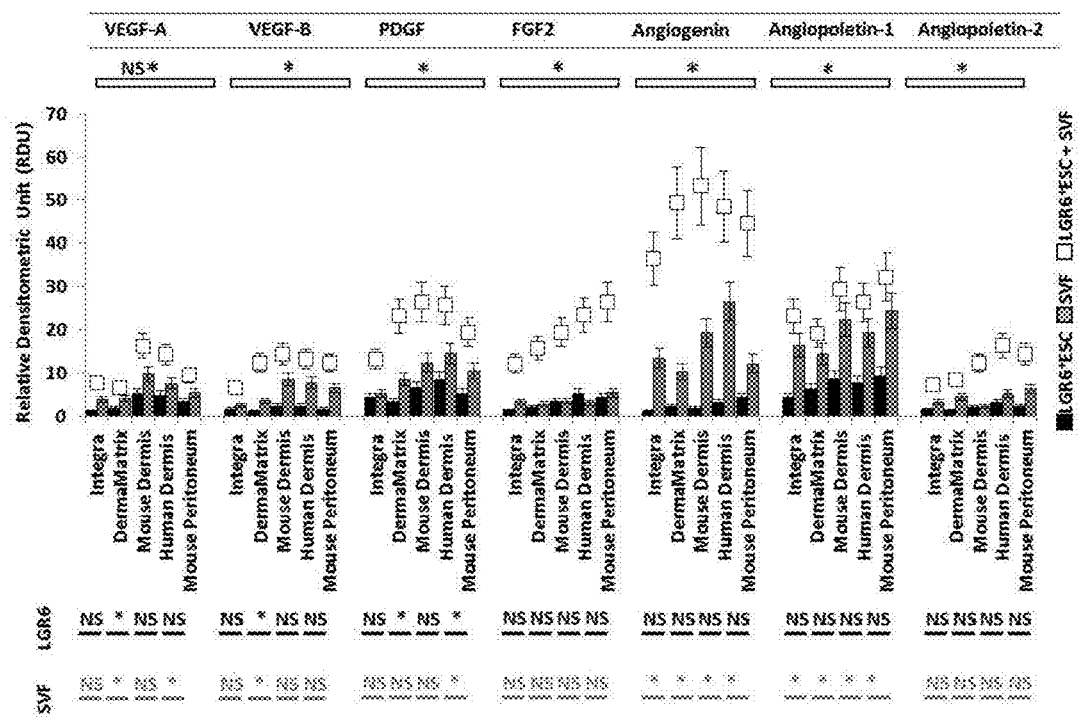

FIGS. 6A and 6B depict an example of a construct containing LGR cells with and without supportive cellular entities and the relative production of growth factors. Correlative Expression Profiles of Pro-angiogenic Transcripts and Protein Analytes from LGR6$^{+GFP}$ ESC and SVF$^{RFP}$ Enriched Scaffolding Culture Constructs. FIG. 6A graphs relative fold transcript expression (ΔΔCT) of indicated gene element from total RNA: LGR6$^{+GFP}$ ESC (black bar), SVF$^{RFP}$ (grey bar), and co-cultured LGR6$^{+GFP}$ ESC+ SVF$^{RFP}$ (white box) on respective scaffold substrate. Significance above the x-axis (LGR6+SVF) indicates the inter-comparison co-cultured LGR6$^{+GFP}$ ESC+SVF$^{RFP}$ expression vs. singular LGR6$^{+GFP}$ ESC and SVF$^{RFP}$ expression on indicated scaffolding. Ex. Average FGF-2 gene expression for co-cultured matrices was higher than the average expression of both singular systems (Scaffold+ LGR6 or scaffold +SVF) except for co-cultured INTEGRA® (INTEGRA®+ LGR6$^+$ SVF). Significance below the x-axis (LGR6) or (SVF) indicates the intra-comparison of substrates, while the cellular entity remains constant. Ex. VEGF-A gene expression for INTEGRA®+ LGR6$^{+GFP}$ ESC only vs. DERMAMATRIX®+ LGR6$^{+GFP}$ ESC only was nonsignificant (NS). FIG. 6B graphically represents the relative densitometric unit (RDU) of indicated protein analyte from total protein isolates: LGR6$^{+GFP}$ ESC (black bar), SVF$^{RFP}$ (grey bar), and co-cultured LGR6$^{+GFP}$ ESC+ SVF$^{RFP}$ (white box) on respective scaffold substrate. (*) indicates (p-value<0.05), assays completed in triplicates, GAPDH housekeeping control.

Figure 7A:
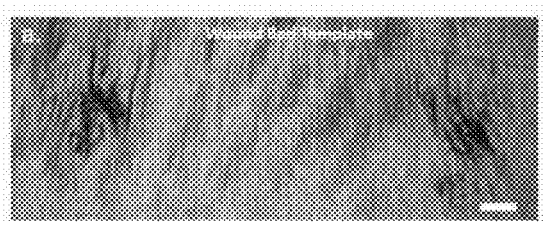
FIGS. 7A-H illustrate third degree wound bed induction and verification of the elimination of the LGR stem cell follicular bulge and adnexal structures.
Figure 7B:
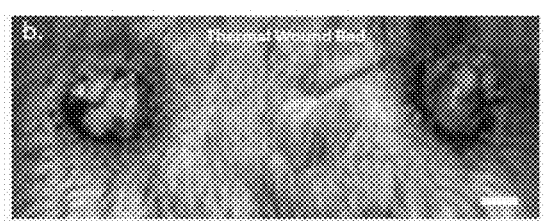
Figure 7C:
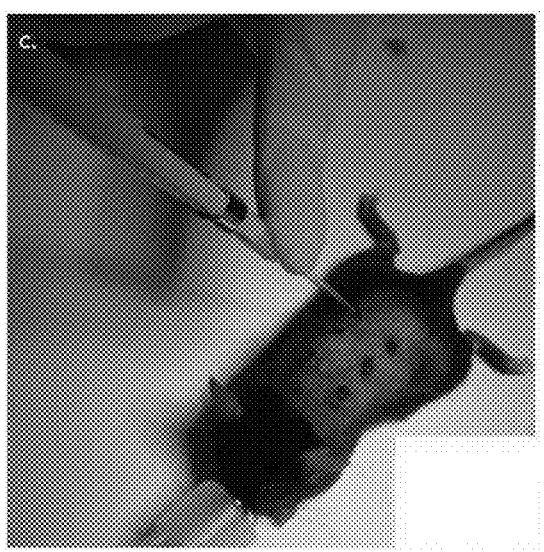
Figure 7D:
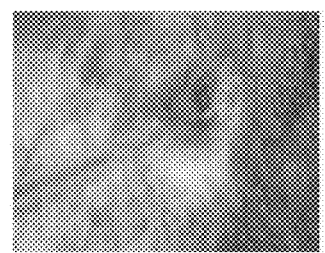
Figure 7F:
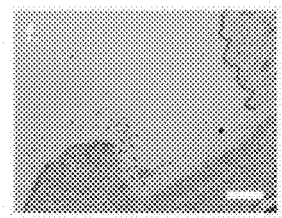
Figure 7E:
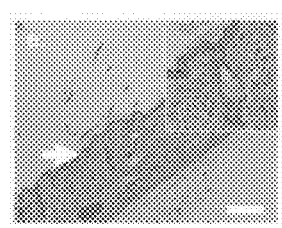
Figure 7G:
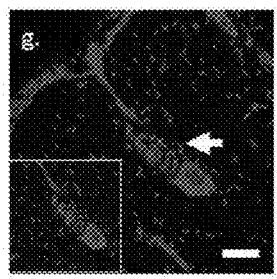
Figure 7H:
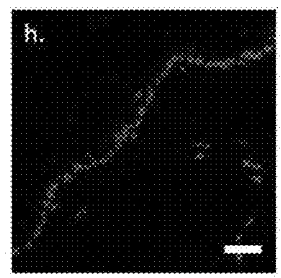

FIGS. 7A-H illustrate a wound/injury/void receiving therapy example of enhanced LGR cell migration, proliferation and viability into a wound namely a third degree wound bed induction and verification of the elimination of the LGR stem cell follicular bulge and adnexal structures. FIG. 7A depicts a wound bed template marks of 3 mm diameter. FIG. 7B depicts the wound bed structure at day 0 (the white scale bar being 1 mm). FIG. 7C illustrates an example of a 2×3 3 mm wound bed grid. FIG. 7D shows topical application of the re-suspended peptide at the wound site. FIG. 7E is a photomicrograph of H&E stain of non-burned, intact Integument/skin with hair follicle and adnexal structures. The arrow indicates the location of the magnified follicle (inset image) where the white scale bar is 500 µm. FIG. 7F is an H&E stain of dorsal murine skin following high temperature cautery depicting removal of epidermal, dermal and hypodermal tissues including the follicular bulge. FIG. 7G is DAPI/DNA stain (4',6-diamidino-2-phenylindole) of non-burned, intact skin with hair follicle and adnexal structures. The arrow indicates the magnified follicle with co-labeling of immunofluorescent LGR5 and LGR6 antibodies green and red respectively (inset image). FIG. 7H DAPI/DNA stain of dorsal murine skin following high temperature cautery depicting removal of epidermal, dermal, and hypodermal tissues including the follicular bulge where the white scale bar is 100 µm.

Figure 8A:
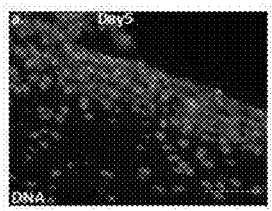
FIGS. 8A-Q depict time progression of a wound/injury/void with DEFA5 as it relates to bacterial adhesion.
Figure 8B:
Figure 8C:
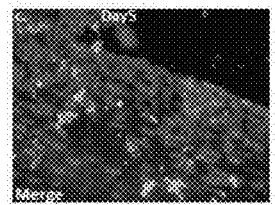
Figure 8D:
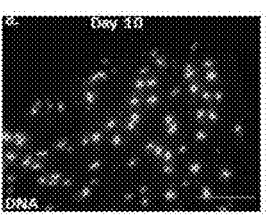
Figure 8E:
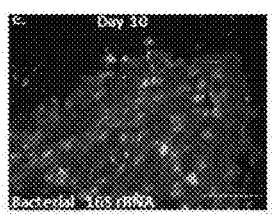
Figure 8F:
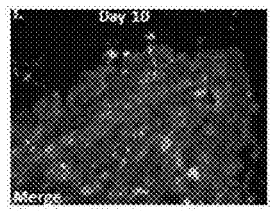
Figure 8G:
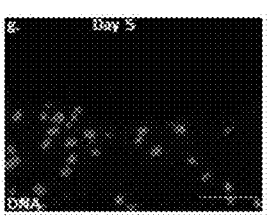
Figure 8H:
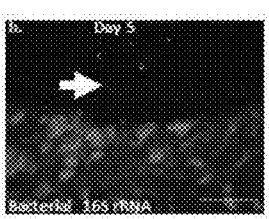
Figure 8I:
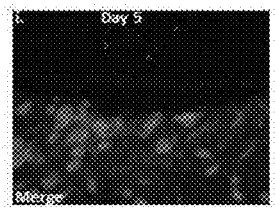
Figure 8J:
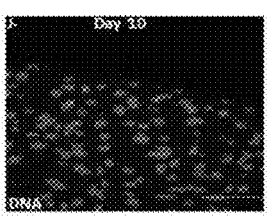
Figure 8K:
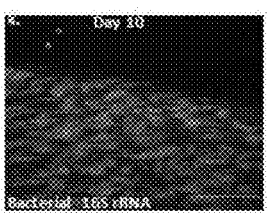
Figure 8L:
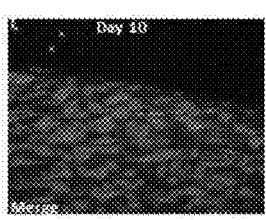

FIGS. 8A-Q depict a wound/injury/void with LGR as it relates to antimicrobial behavior over five and ten day time periods. Using 16S rRNA fluorescent oligonucleotide probes, in-situ hybridization indicates the presence of bacterial adhesion at the third degree burn wound bed. FIG. 8A presents DNA/DAPI labeling of a 3rd degree burn wound bed at day five post burn induction treated daily with SDZ. In FIG. 8B 5'-Cy3-EUB338 labeled 16s rRNA of 3rd degree burn wound bed bacterial organisms (yellow grains) at day five post burn induction treated daily with SDZ are depicted. FIG. 8C is a digitally merged image of FIGS. 8A and 8B. FIG. 8D corresponds to FIG. 8A except at day ten with DNA/DAPI labeling of 3rd degree burn wound bed treated daily with SDZ. Correspondingly, FIG. 8E is a photomicrograph of the 5'-Cy3-EUB338 labeled 16s rRNA of 3rd degree burn wound bed bacterial organisms (yellow grains) at day ten post burn induction treated daily with SDZ. FIG.

8F is a merged image of FIGS. 8D and E. FIGS. 8G-8L are images corresponding respectively to the five and ten post burn periods of FIGS. 8A-F but subject to daily treatment using Defensin, alpha 5 (DEFA5) rather than SDZ. The arrow in H represents the interface of tissue with overlying fibrinous material where less bacteria is observed in the setting of DEFA5 treatment.

FIG. 8M with inset 8N demonstrate quantification of white pixel intensity of Cy3 fluorescence grayscale converted image of a wound bed treated with SDZ and containing more 16s rRNA labeling per unit area. FIG. 8O and inset 8P correspondingly show quantification of white pixel intensity of Cy3 fluorescence grayscale converted image of (inset image p.) a wound bed treated with DEFA5 and containing a reduced 16s rRNA labeling per unit area. The inset graph depicts averaged white pixel intensity of 16s rRNA expressed in both SDZ and DEFA5 treated burn wound beds at day five using grayscale imaging software. Finally, FIG. 8Q is a graph to illustrate averaged red channel fluorescence of 16s rRNA expressed in both SDZ and DEFA5 treated burn wound beds at day five. The white arrow in FIG. 8H indicates potential film in DEFA5 treated wound beds and the black arrow in FIG. 8M indicates white pixel intensity. Scale bar 100 μm. (*) indicates p-value <0.05.

Figure 9A:
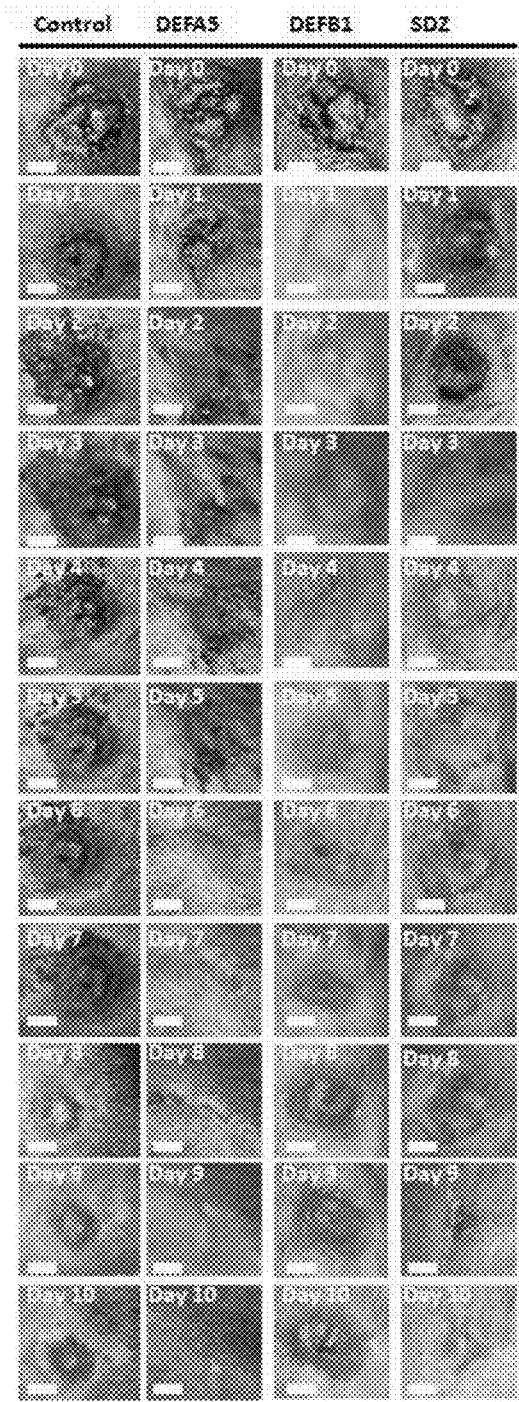
FIGS. 9A and B are comparative photographs of DEFA5 expressing cellular entities within a wound bed as it relates to augmented healing, tissue and appendage regeneration and subsequent hair growth in treated burn wounds devoid of adnexal structures.
Figure 9B:
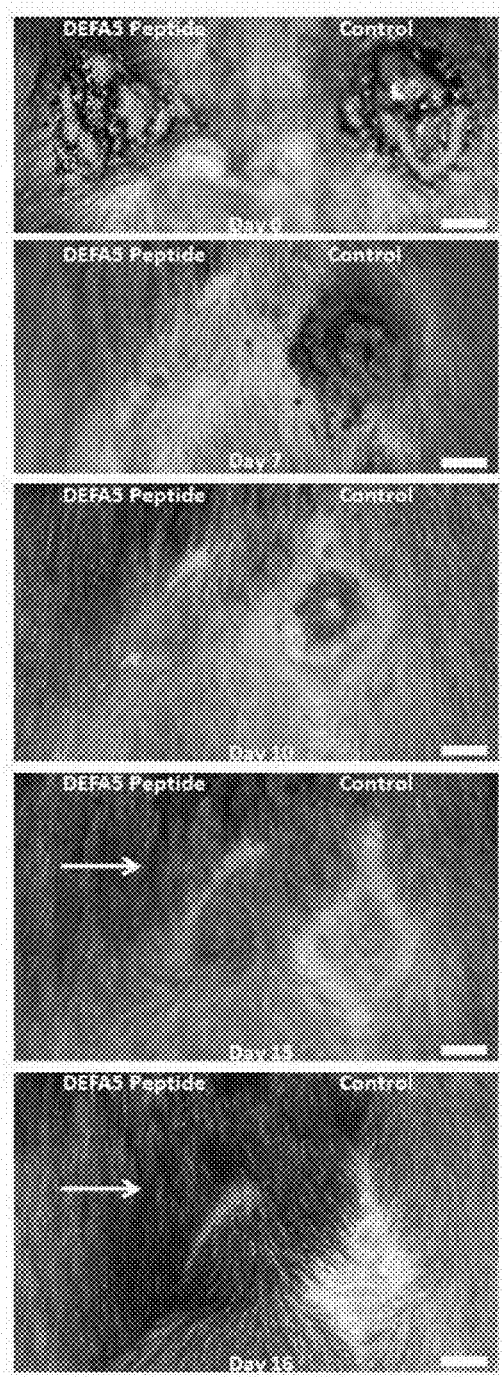

FIGS. 9A and B are a series of time progression photographs that represents an example of LGR expressing cellular entities within wound as it relates to augmented healing, tissue and appendage regeneration and subsequent hair growth, wound healing kinetics and nascent hair growth in treated burn wounds devoid of adnexal structures. The photographic series comprising FIG. 9A are gross imaging using a Leica Wild M680 surgical microscope to image healing of 3rd degree burn wound beds over 10 days while being treated with indicated agents MQH2O, DEFA5, DEFB1, SDZ. The white scale bar represents 1 mm. The second photographic series of FIG. 9B again comprises gross imaging using a Leica Wild M680 to track nascent hair growth of 3rd degree burn wound beds over 16 days in a side by side comparison of DEFA5 vs. control treated wound beds. The white arrows indicate the growth of new hair. Again, the scale bar is 1 mm.

Figure 10A:
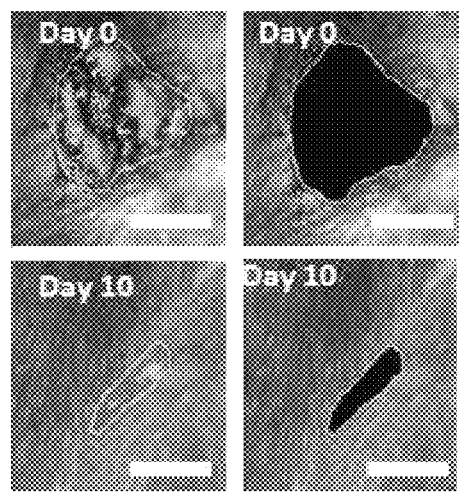
Figure 10B:
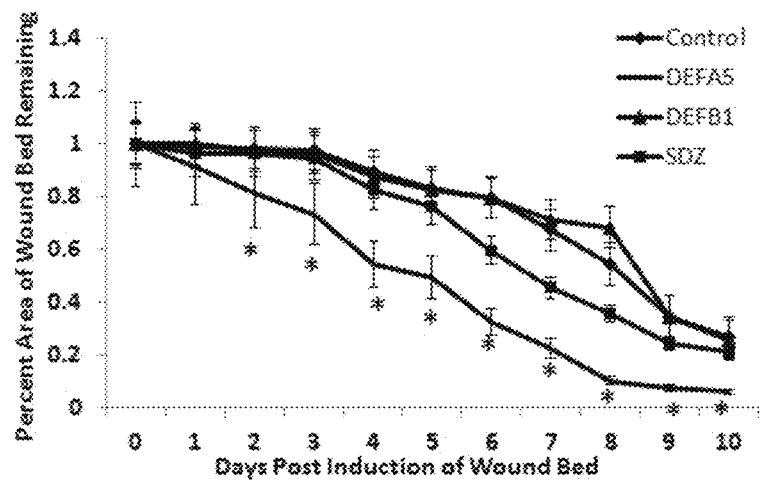
Figure 10K:
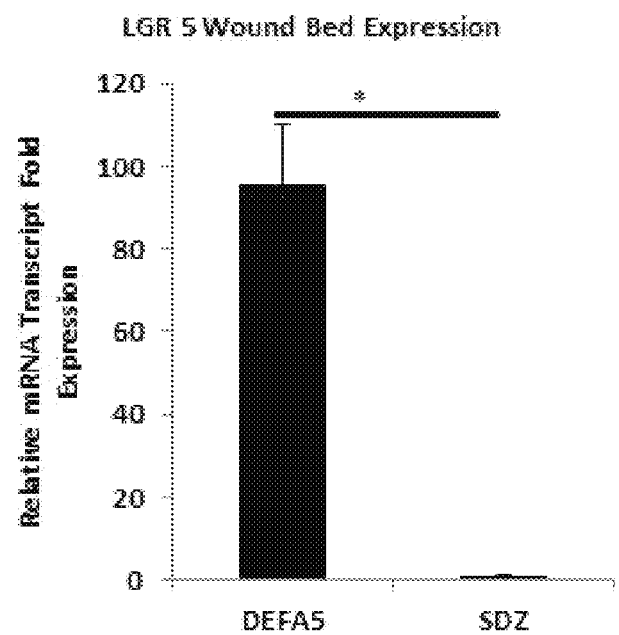
Figure 10L:
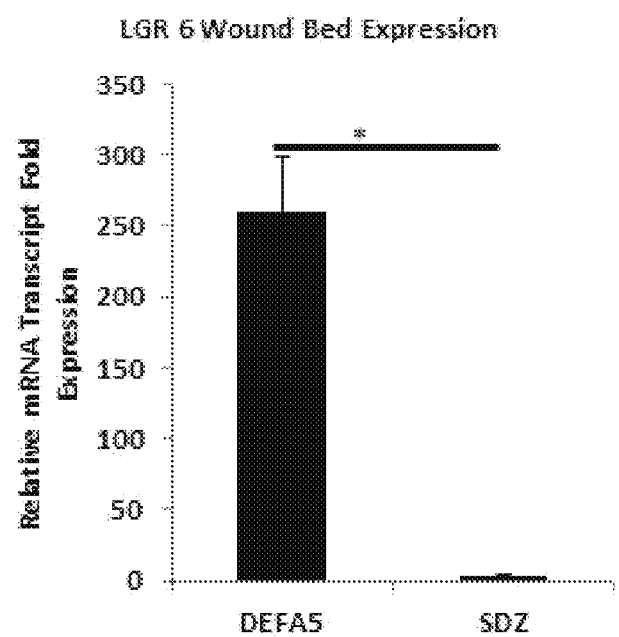

FIGS. 10A-L comprise an example of said LGR expressing cellular entities within wound/injury/tissue void as it relates to augmented healing, propagation of said entities. The Graphs comprising FIGS. 10K and 10L provide evidence of quantification of wound bed healing kinetics and LGR5 and LGR6 stem cell migration into burn tissue following treatment with topical focal agents. Briefly, these tests were used to confirm the quantitative confocal microscopic intensity patterns from imaging LGR5 and LGR6, and based on reverse-transcriptase polymerase chain reaction on burn wound tissues. As represented in the graphs, averaged LGR5 and LGR6 mRNA expression within human alpha defensin 5 wound beds was found to be 95.8±10.6 and 259.2±20.2, respectively, compared with undetectable levels of LGR5 and LGR6 in sulfadiazine-treated wounds at day 5 (FIG. 4, right). The magnitudes of these fold-level comparisons within human alpha defensin 5-treated tissues and those specimens treated with sulfadiazine suggest that it is the absolute presence or void of cells expressing LGR5 and LGR6 migrating into the wound that defines the fold values.

Turing to the specific figures, FIG. 10A presents photographs of a wound area with a white scale bar representing 1 mm and the wound area calculation in black. FIG. 10B graphically displays the averaged wound healing rate expressed as percent % of wound area remaining over 10 day period of indicated topical focal agent application. The asterisk (*) represents a p-value <0.05. FIGS. 10C-J are LGR5 and LGR6 immunofluorescent antibody labeling of a DEFA5 treated wound bed at day 5 where FIG. 10C is DNA/DAPI/Blue, FIG. 10D is LGR5/FITC/Green FIG. 10E is LGR6/TRITC/Red and FIG. 10F is a merger of 10C-10E. FIGS. 10G-I are corresponding LGR5 and LGR6 immunofluorescent antibody labeling of SDZ (sulfadiazine) treated wound bed at day 5 (DNA/DAPI/Blue, LGR5/FITC/Green and LGR6/TRITC/Red). FIG. 10J is a merged image of 10G-10I and includes an inset representing averaged LGR5 and LGR6 expression using Green and Red fluorescent intensity per wound bed at day 5. The comparative values obtained from Reverse Transcriptase PCR quantification of the fold increase in RNA extracted from replicate wound beds treated with DEFA5 and SDZ is set out. The white scale bar 50 μm and again, the asterisk (*) represents a p-value <0.05.

Figure 11A:
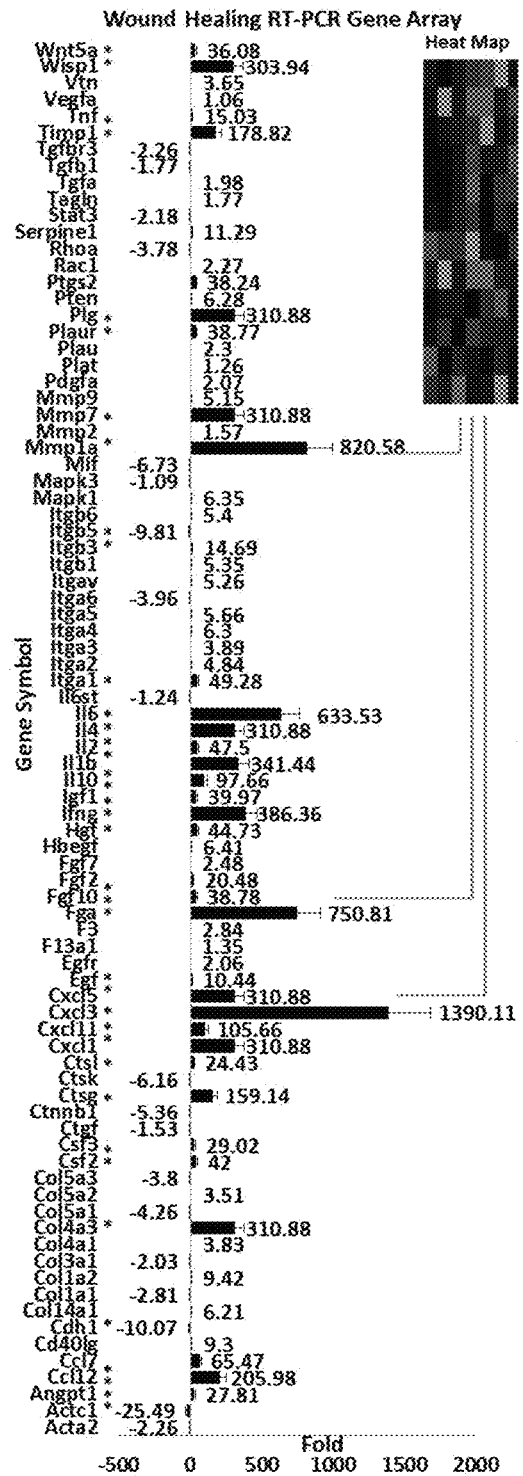
FIGS. 11A and B illustrate RT-PCR quantification and gene heat mapping comparison of wound/injury/tissue voids treated with DEFA5 to SDZ as it relates to augmentation of pro-healing pathways.

FIGS. 11A and B illustrate a wound/injury/tissue void with the LGR expressing cellular entities placed within wound as it relates to augmentation of pro-healing pathways. The figures respectively represent RT-PCR quantification and gene heat mapping comparison of wound beds treated with DEFA5 to SDZ. These figures show the role of human alpha defensin 5 versus sulfadiazine in augmenting key transcript expression within the wound. The results show that several gene subsets are significantly up-regulated within the wound beds receiving human alpha defensin 5 when compared with sulfadiazine therapy and that certain Wnt pathway gene subsets are significantly up-regulated in response of the LGR stem cell system to Wnt ligands in both the gut and skin.

Figure 11B:
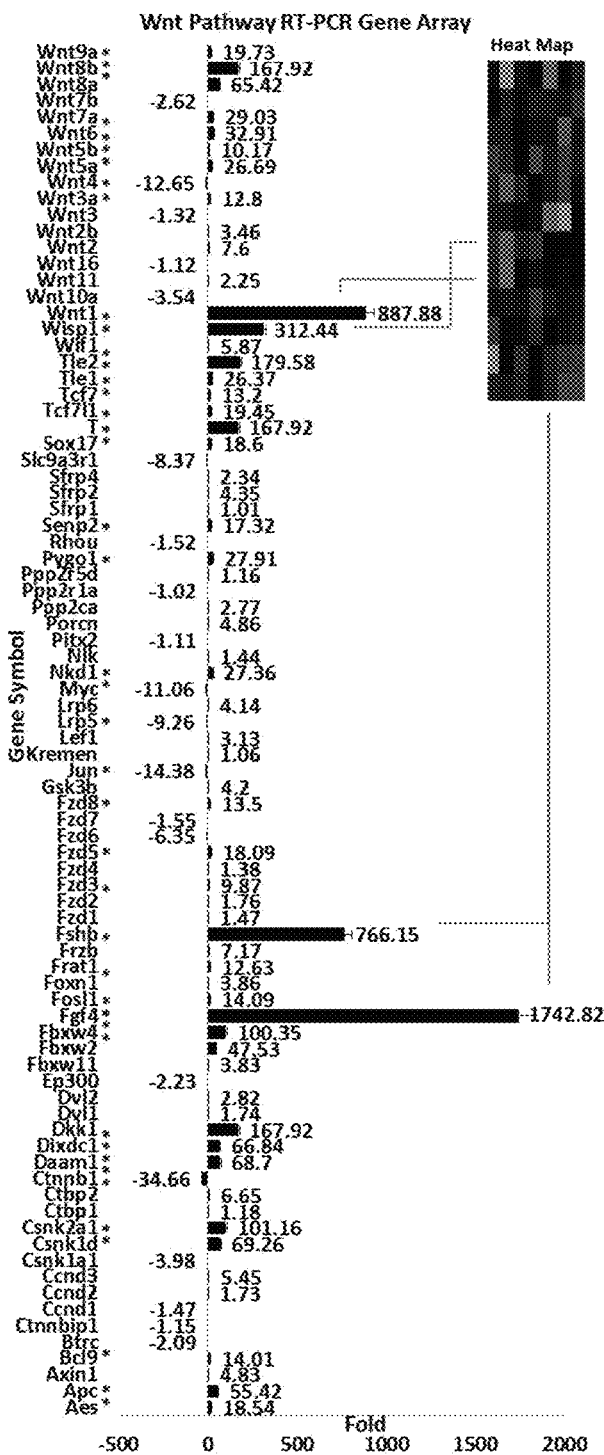

FIG. 11A presents an Averaged Wound Healing RT2-PCR Array pathway heat map and corresponding gene map with fold regulation for wound beds comparing DEFA5 to SDZ treated systems. FIG. 11B presents an Averaged Wnt RT2-PCR Array healing pathway heat map and corresponding gene map with fold regulation for wound beds comparing DEFA5 to SDZ treated systems. The colors of the heat maps are indicated as red, more expressed in DEFA5 treated burns to green more expressed in SDZ treated burns.

FIGS. 12A-I represent an example of a micro-aggregate multicellular unit containing LGR expressing stem cell foci as it relates to location, population identity and wound healing capacity. Using a simple ex vivo wound healing assay and fluorescence-activated cell sorting, LGR6+, CD34+, and CD73+C57BL/6(UBC-GFP) murine cells were isolated for cell culture expansion.

FIG. 12A depicts LGR6 fluorescent antibody (green) expression of cells on the hair follicle following partial epidermal 10 unit/μL dispase digestion. (Worthington Biochemical Corp., Lakewood, N.J.) digestion for 30 minutes at 37° C. on a slow rocker. FIG. 12B is of LGR6+ cells expressing additional CD34 and CD73 markers (the arrow indicates population isolated comprising approximately 1 to 3 percent of all cells). FIGS. 12C-H are eFluor450 expression histograms of an in vitro wound assay respectively showing periodic intrinsic GFP expression from C57BL/6 (UBC-GFP) murine cells, CD34+PE/Cy7 expression, LGR6+ APC expression and CD73+. The dotted lines indicates the distance of separation at 0, 6, and 12 hours following disruption of the cell layer and the scale bar=50 μm. The graph of FIG. 12I sets out the averaged reduction in the distance line over time expressed as a percentage of initial distance following fluorescence sorting where the asterisk (*) represents a p-value <0.05.

FIGS. 13A-D are photomicrographs by confocal microscopy and bioluminescence of an activated functional singularity unit (aFSU) at the time initial seeding and 1 day later showing an example of a micro-aggregate multicellular unit containing LGR expressing stem cell foci while undergoing initial propagation on a collagen matrix, FIG. 13 E.

Figure 14A:
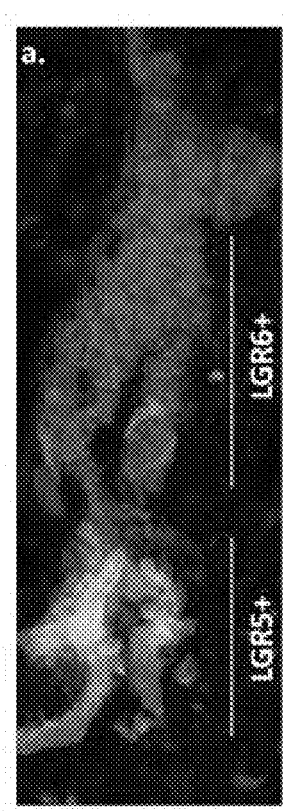
FIGS. 14A-E depict an example of location LGR cellular varieties as it relates to location, phenotype, interface and polarity within a cutaneous tissue. Isolation and culture of the LGR6+ ESC from the follicular bulge.

FIGS. 14A-E depict an example of location LGR cellular varieties as it relates to location, phenotype, interface and polarity within a cutaneous tissue. FIG. 14A shows by Immunofluorescence staining, localized regions of LGR6 (Green/fluorescein isothiocyanate (FITC)) and LGR5 (Red/tetramethyl rhodamine isothiocyanate (TRITC)) expression. The scale bar is for 20 µm.

Figure 14B:
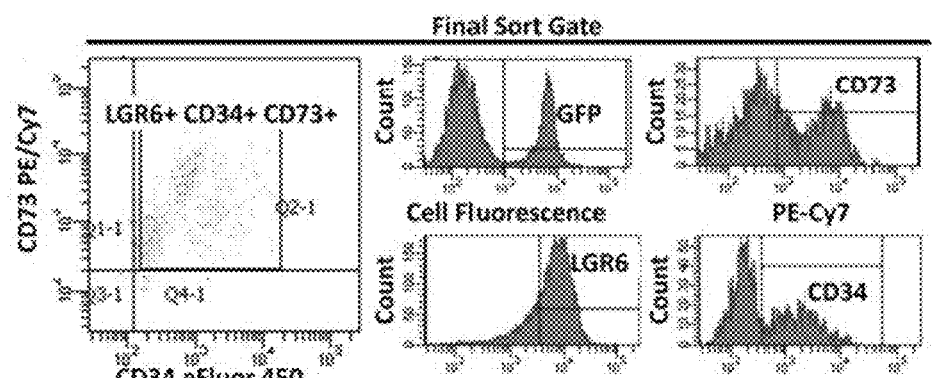
Figures 14C, 14D, 14E:
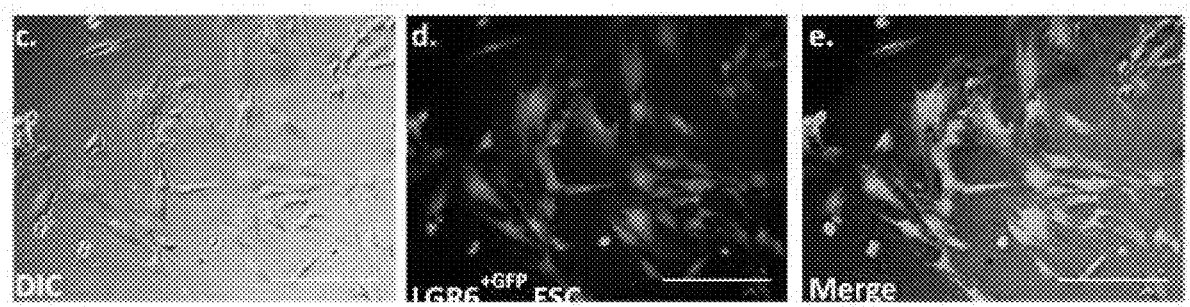

FIG. 14B shows fluorescence-activated cell sorting isolation of the LGR6+$^{GFP}$ epithelial stem cells from C57BL/6(UBCGFP) murine skin with the final sort gate using LGR6+, CD34 and CD73 on the left and individual histograms depicting cellular GFP expression and correlating antibody-conjugate labels: CD73/PE-7, LGR6/Cy5, CD34/eFlour450 on the right. FIG. 14C shows differential interference contrast image of LGR6+$^{GFP}$ epithelial stem cells plated following fluorescence-activated cell sorting isolation. FIG. 14D depicts intrinsic GFP expression of the LGR6+$^{GFP}$ epithelial stem cells and FIG. 14E is a merged image of FIGS. 14C and 14 D. The scale bar represents 20 µm.

FIGS. 15A-E provide an example of LGR expressing cellular foci as it relates to a method of delivery through placement around and/or within wound/injury/tissue void. The three images of FIG. 15A depict, respectively, an initial burn template; a full thickness burn on the dorsum on Nu/Nu mouse; and delivery of HYDROGEL® containing $10^5$ LGR6+$^{GFP}$ epithelial stem cells at the base of the wound bed. The scale bar for FIG. 15A is 1 mm. FIG. 15B is an immunofluorescece image of the injection pocket DNA/DAPI-BLUE at Day 0 FIG. 15B is an immunofluorescece image of anti-LGR6/TRITC antibody labeling and FIG. 15C the same for LGR6+$^{GFP}$ epithelial stem cells. FIG. 15 E is a merged image of FIGS. 15B-D and has a scale bar of 20 µm. FIGS. 15A-E show full thickness burn wound bed induction and validation of LGR6+ stem cell engraftment into subsequent soft tissue defect.

Figures 16A, 16C, 16D:
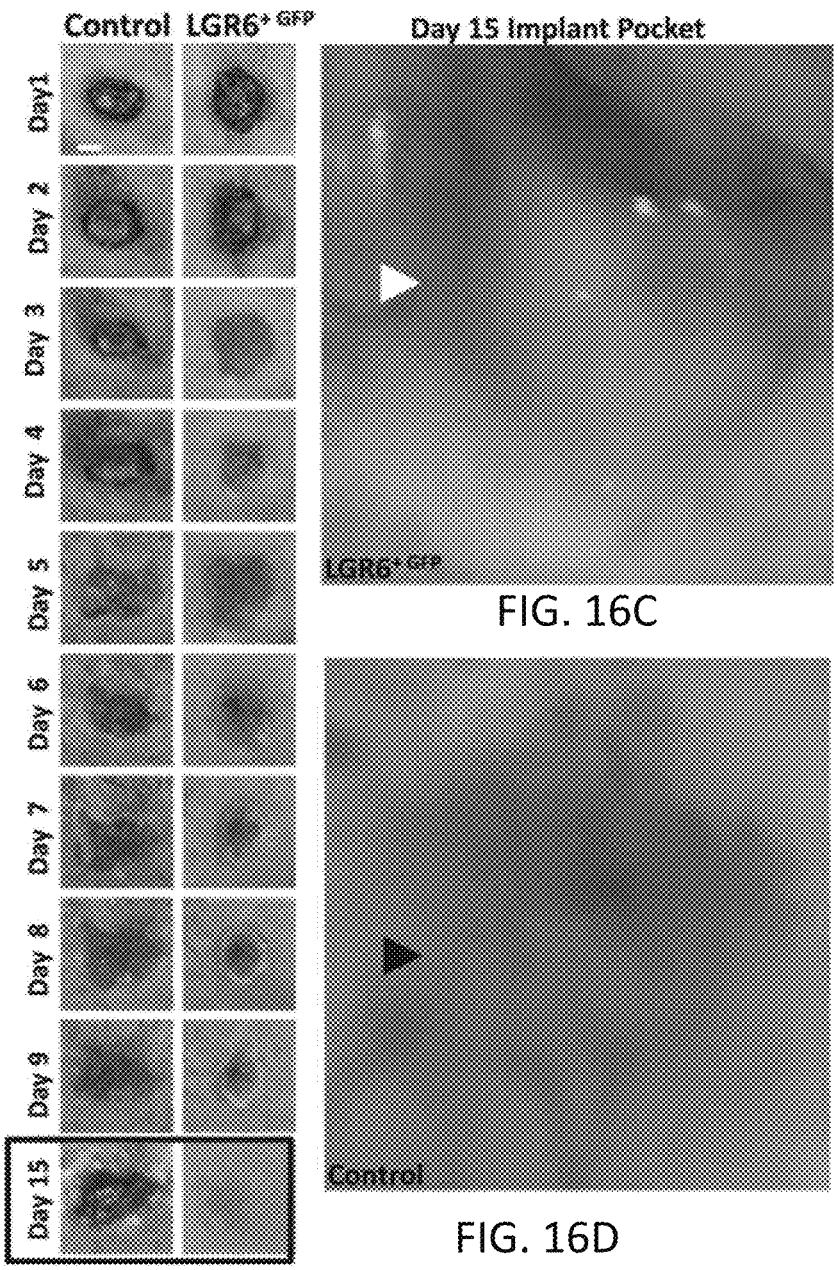

FIGS. 16A-D depict an example of LGR containing stem cell focus as it relates to delivery into and around wounds via a deliverable vector and subsequent healing, regeneration of tissues and supporting structures including but not limited blood vessel angiogenesis and/or angiogenesis. Wound healing progression following LGR6+ epithelial stem cells transplantation into full thickness wounds. The progression of wound healing is depicted following the injection of HYDROGEL® from BD Biosciences, San Jose, Calif. (control) in FIG. 16A compared with FIG. 16B, LGR6+$^{GFP}$ epithelial stem cells seeded HYDROGEL® over 15 days. The scale bar is 1 mm. In FIG. 16C, showing the implant pocket after day 15, the white arrow indicates presence of a remaining LGR6+$^{GFP}$ epithelial stem cells population located within healing wound bed. In FIG. 16D, the black arrow indicates the location of the burn wound base free of LGR6+$^{GFP}$ epithelial stem cells.

Figure 17A:
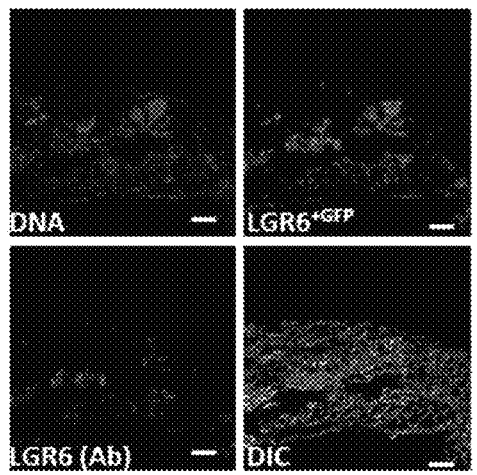
FIGS. 17A-D show LGR6+ epithelial stem cell migration and differentiation within full-thickness wound beds 10 days after transplantation.

FIGS. 17A-D depicts an example of LGR containing stem cell focus following delivery into and/or around wound with subsequent healing and regeneration of tissues and related appendages such as but not limited to hair follicle and related supportive structures. FIG. 17A is a four panel matrix of confocal images of immunofluorescent labeled tissue specimen at day 10 following transplantation of LGR6+ epithelial stem cells migration into the wound bed 10 days. The images comprising FIG. 17A include DNA/DAPI-BLUE; anti-LGR6/TRITC; GFP expression of LGR6+$^{GFP}$ ESC.

Figure 17B:
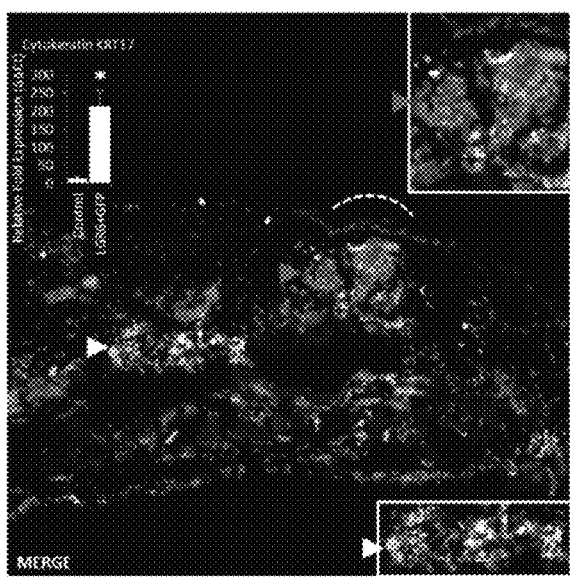

FIG. 17B is a differential interference contrast image merge of all channels. The Red arrow designates regions of nascent follicle development. (See also the upper inset image). The dotted line shows epithelial polarization overlying nascent hair follicles while the white arrow indicates the location of the graft injection pocket (See also the magnification thereof in the lower inset image for an image of the initial injection pocket cellular population. The inset graph of FIG. 17B represents comparative KRT17/cytokeratin 17 gene expression within the indicated wound beds of the control and LGR6+$^{+GFP}$ treatment.

Figure 17C:
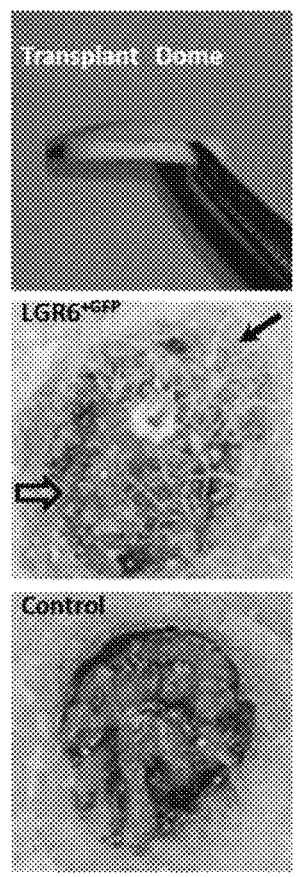
Figure 17D:
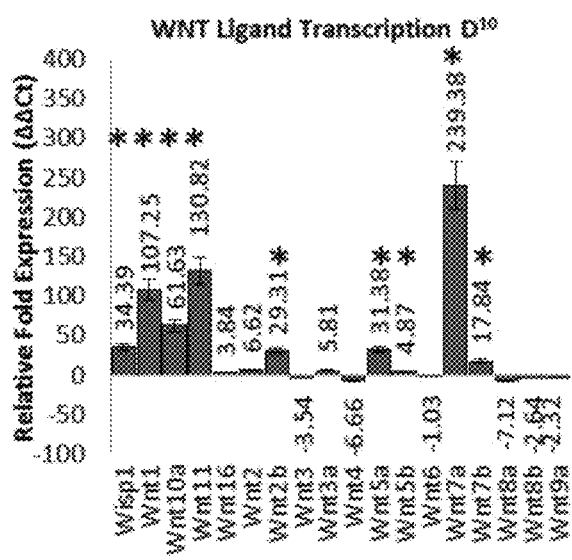

Referring to FIG. 17C, the three images are of a Transplant dome used to cover hair follicle study population burn wound beds, an LGR6+$^{+GFP}$ ESC treated wound bed at day 10 (solid arrow) with nascent hair follicles (clear arrow) follicle cyst formation and a control wound bed at day 10. The graph comprising FIG. 17D quantifies the Day 10 wound bed resulting from RT-PCR indicating relative gene fold expression of WNT ligands. The positive numbers indicated higher expression in LGR6+$^{GFP}$ epithelial stem cells wound beds while the negative numbers indicate higher expression in control wound beds.

Figure 18:
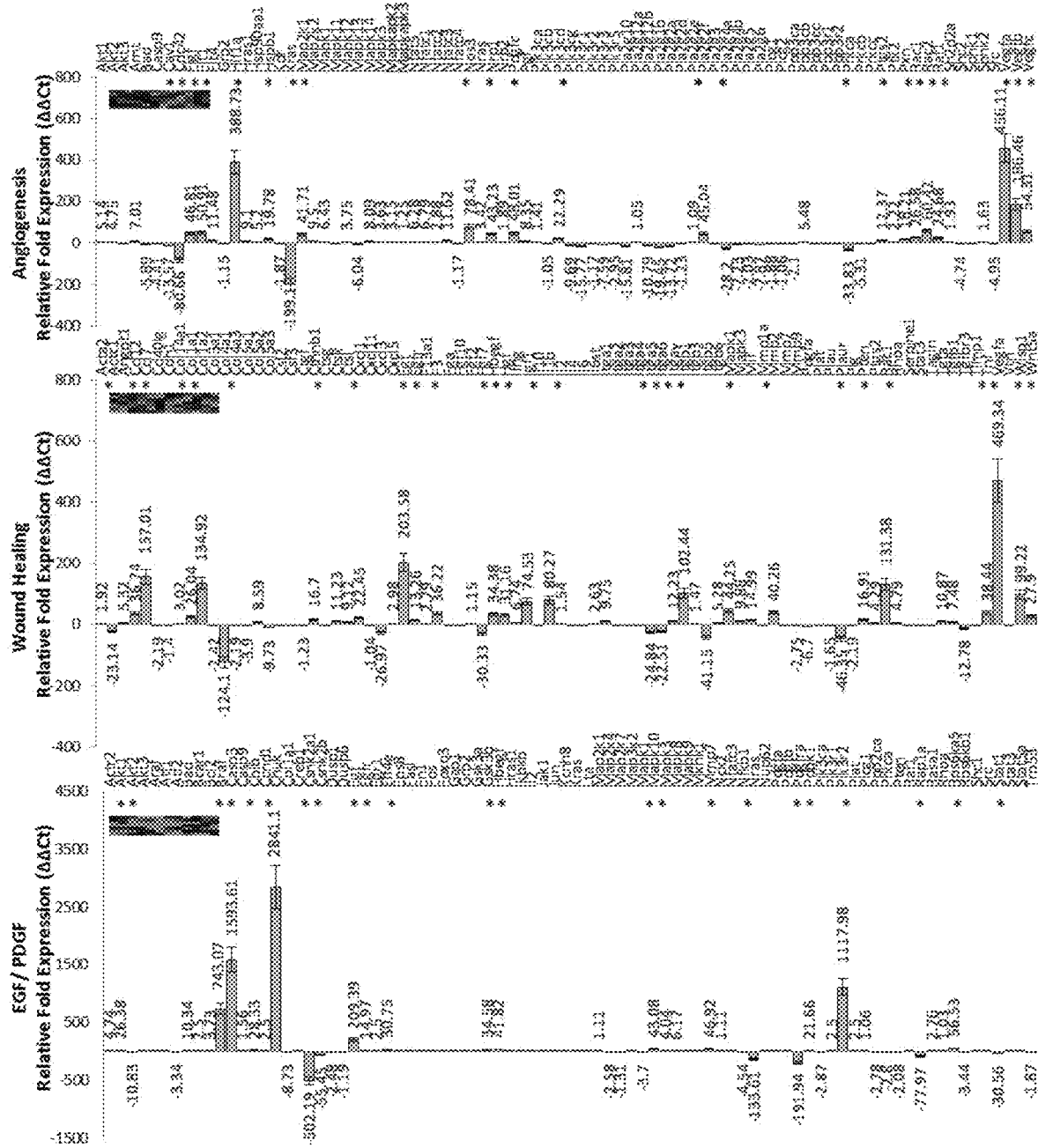
FIG. 18 provides an RT-PCR quantification and inset gene heat mapping comparison of a wound/injury/tissue void with the LGR expressing cellular foci.

FIG. 18 provides an RT-PCR quantification and inset gene heat mapping comparison of a wound/injury/tissue void with the LGR expressing cellular foci as it relates to delivery into and/or around wound/injury/tissue void as it relates to augmentation of pro-healing pathways and comparative gene expression of wounds receiving LGR6+ epithelial stem cells against a control. The graphs illustrate the relative fold expression of genes for angiogenesis, wound healing and epidermal growth factor. Correlative graphical representation of data comparing wound beds receiving LGR6+ epithelial stem cells and control therapy. As to the inset heat maps the color red indicates greater expression within the LGR6+ epithelial stem cell wound bed while the color green indicates greater expression within the control wound bed. In the bar graphs, positive numbers indicated higher expression in LGR6+$^{GFP}$ epithelial stem cell wound beds and negative numbers indicate higher expression in control wound beds. The NCBI Unigene term is indicated at the top of each quantitative column and the asterisk (*) P-value designates <0.05 significance.

Figure 19:
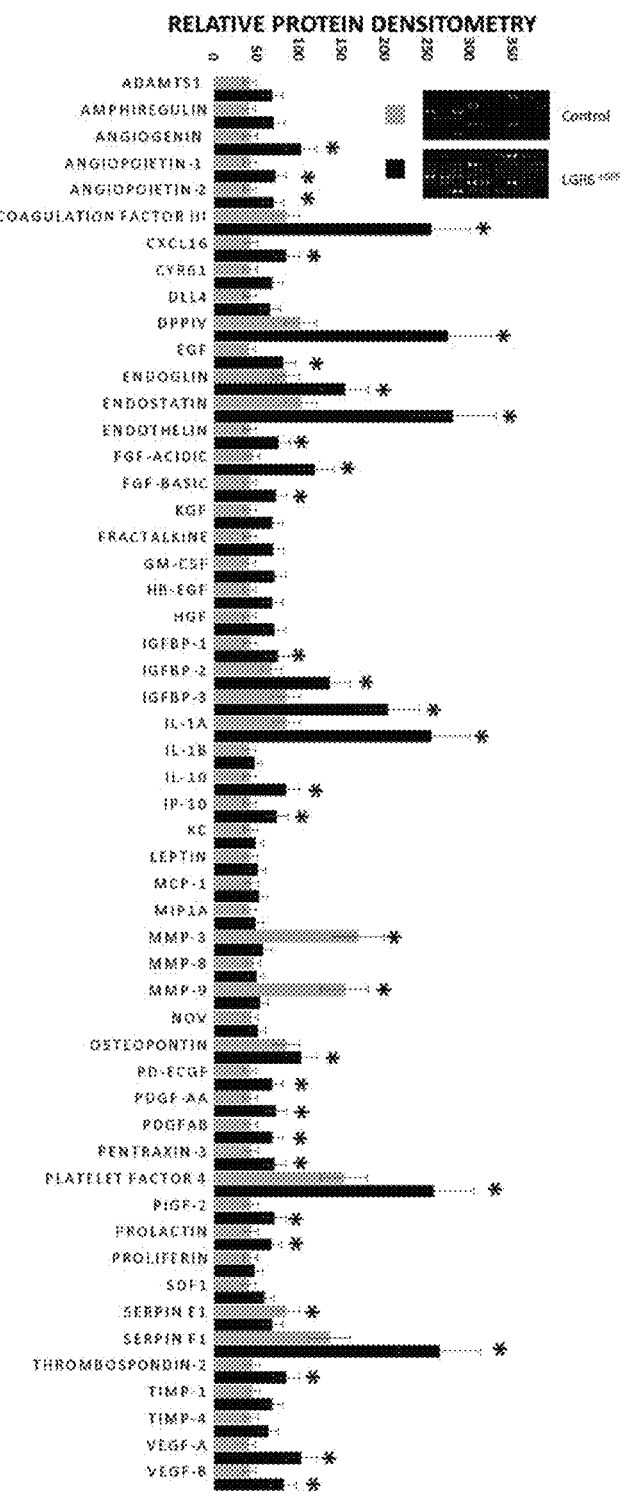
FIG. 19 depicts an example of said LGR expressing cellular foci as it relates to delivery into and/or around wound/injury/tissue void and augmentation of wound healing factors.

FIG. 19 graphically presents the relative protein densitometry of an example of LGR expressing cellular foci as it relates to delivery into and/or around wound/injury/tissue void and augmentation of wound healing factors. Comparative angiogenesis analyte expression of wounds receiving LGR6+ ESCs Proteomic array comparing common proteins which regulate and augmented angiogenesis. The grey columns indicate control wounds and the black columns indicated those wounds that received the LGR6+$^{GFP}$ ESC. The inset image shows example proteome array membranes following development with HRP chemi-luminesce. Brighter colors indicate higher levels of protein expression.

Figure 20A:
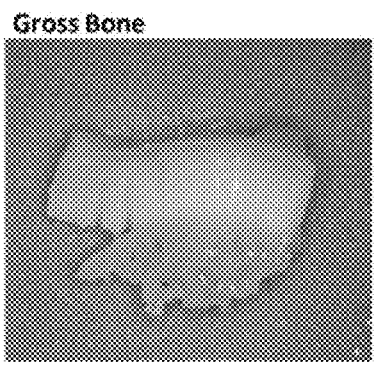
FIGS. 20A-F illustrate an example of LGR expressing cellular foci as it relates to the regeneration of bone tissues. Isolated LGR foci can be seeded bone and remain viable.
Figure 20B:
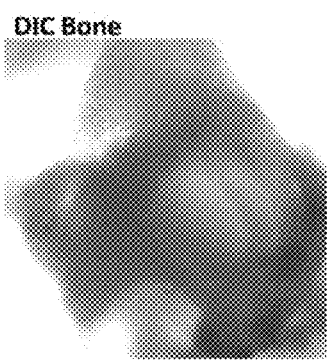
Figure 20C:
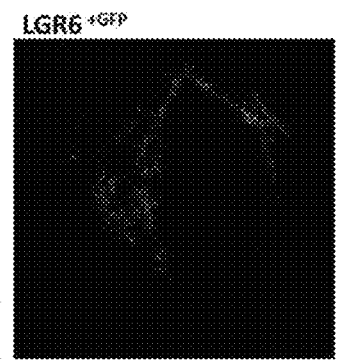
Figure 20D:
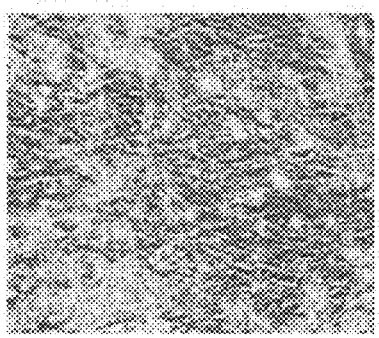
Figure 20E:
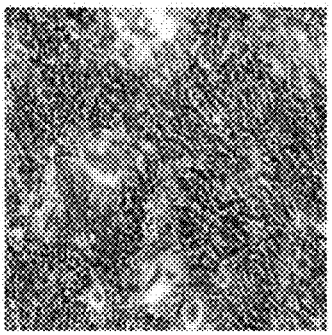
Figure 20F:
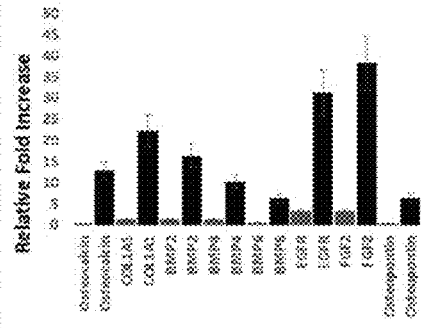

FIGS. 20A-F illustrate an example of LGR expressing cellular foci as it relates to the regeneration of bone tissues. Isolated LGR foci can be seeded bone and remain viable. FIG. 20A is a gross bone image of harvested bone for culture. FIG. 20B is a DIC image of bone containing LGR GFP 7 days following seeding. FIG. 20C is a 488 nm Green laser confocal image of bone containing LGR6+$^{GFP}$ 7 days following seeding. It is notable that the LGR foci can undergo osteo-induction in-vitro. FIG. 20D depicts LGR foci following 1 week of osteo-induction with supplemental media. FIG. 20E is an Alizarin red stain of the LGR foci following osteo-induction which can undergo osteo-induction in-vitro and up regulate key osteogenic genes. Finally, FIG. 20F is RT-PCR data showing relative fold gene expression where the grey columns represent (control) non-osteo induced LGR and the black columns represent those LGR which received osteo-induction media following 7 days of culture. GAPDH was used as reference standard housekeeping gene.

EXEMPLARY PROTOCOL

The following is a series of examples providing an illustrative protocol sequence for practice of an embodiment of the invention.

Prior to generation of the minimally polarized functional units in accordance with the invention, a gelatinous support such as an exemplary three dimensional collagen scaffold can be generated by well-known processes as follows:

i. Slowly adding 1 part of chilled 10×PBS of 10× culture media to 8 parts of chilled collagen-based solution with gentle swirling. Adding ECM and viability proteins to the suspension;

ii. Adjusting the pH of mixture to 7.2-7.6 using sterile 0.1M NaOH and monitoring the pH adjustment carefully;

iii. Adjusting the final volume to a total of 10 parts with sterile molecular grade water;

iv. Maintaining temperature of mixture at 2-10° C. to prevent gelation, v. Forming a gel by warming to 37° C. for approximately 90 to 120 minutes;

vi. Perforating the scaffold with a sterile micro-needle press (the scaffold can undergo freeze drying process if needed for storage).

It is also recommended that an additional material referred to as Pulse Rescue Media (PRM) be produced and be available prior to commencement of the LGR aggregate extraction procedures.

The PRM, in this embodiment which is direct to humans, is a cell sustaining, serum-free, media mixture Keratinocyte-SFM containing L-glutamine supplied with separately packaged prequalified human recombinant Epidermal Growth Factor 1-53 (EGF 1-53) and Bovine Pituitary Extract (BPE) sold as Keratinocyte-SFM (1×) from Thermo Fisher Scientific to which the antibiotic-antimycotic agents penicillin, streptomycin, and amphotericin B are added along with a GMP- fibrinogen: human. The agent used in one embodiment is GIBCO® Antibiotic-Antimycotic from Thermo Fisher Scientific, a solution containing 10,000 units/mL of penicillin, 10,000 μg/mL of streptomycin, and 25 μg/mL of FUNGIZONE® Antimycotic.

Because the PRM is used to transport human tissues, the supplemental reagents are utilized to stabilize the primary tissues and reduce the viability of micro-organisms during transport and processing.

The following relates specifically to the generation and preservation of LGR expressing epithelial containing stem cell micro-aggregate functional units in accordance with an embodiment of the invention.

Example 1

Example 1 concerns a method for extraction of minimally polarized functional units in accordance with an embodiment of the invention. After obtaining a specimen, it is removed from its associated transport container followed by:

i. Placing the specimen into a sterile 50 ml conical tube containing pulse rescue media and placed on rocker for 5 minutes, repeat with fresh media and container for total of three times;

ii. Removing and placing the specimen into a sterile culture dish containing pulse media and excise fat and hypodermal elements from the dermal and epidermal compartments carefully. Follicular units are left in place and are not overly dissected;

iii. Placing excised hypodermal fat components into separate a 50 ml conical tube containing PRM and place in +4° C. on slow rocker.

iv. Sectioning the remaining cutaneous elements containing epidermal, follicular and dermal compartments into minimal polarized functional units (MPFUs) using ultrafine-WECPREP® Blades or some form of micro-16 lancet; and v. Placing the MPFUs components into separate a 50 ml conical tube containing pulse media and place in +4° C.

The following relates to secondary processing where the primary cultures are established and functional tissue elements are prepared utilizing enzymatic preparation using conventional CLIA equipment and reagents meeting FDA and/or GMP certification:

Example 2

Example 2 is directed to processing of hypodermis and subdermal fat cellular components. Example 2 recites the following steps:

i. Spraying 70% ethanol (EtOH) on the outer side of the tissue container and placing the tissue container into laminar air flow cabinet;

ii. Sending a sample of the tissue or transfer medium for microbiological testing;

iii. Placing the previously washed adipose and hypodermal tissue in 150 mm sterile petri dish;

iv. Washing the tissue two times with PRM;

v. Trimming the tissue into small (3 mm) pieces with sterile surgical instrument and place into sterile culture holding dish containing pulse media while the dissection is completed;

vi. Aspirating media from holding dish and removing the specimen with sterile scoop or forceps followed by placing the specimen into 50 ml conical tube containing MSC Enzymatic Digestive Media, a pre-mixed digestive enzyme solution (collagenase and dispase-based), which is placed into a 37° C. water bath or dry heat slow shaker and shaken for 30 minutes or until there are few particulate materials remaining;

vii. Adding 37° C. phosphate buffer saline (PBS) ethylenediamine tetraacetic acid (EDTA) (equal volume PBS-EDTA) to stop the digestion;

viii. Centrifuging the suspension for 10 minutes to generate a "soft" pellet;

ix. Discarding upper liquid portion and using a sterile pipette, separating the adipose population from stromal vascular fraction (SVF) in the saved mass;

x. Re-suspending the SVF in phosphate buffer saline/EDTA, PBS-EDTA (1 mM of EDTA), and re-suspending adipocyte population in PRM in two separate conical tubes;

xi. Using 100 μm sterile, filter the suspension into new sterile conical tubes;

xii. Washing the filter with PBS-EDTA;

xiiiv. Spin filtering the suspension for 10 minutes at room temperature followed by aspiration of the media and replacing the aspirated media with a known volume of fresh media;
xiv. Using a COUNTESS® automated cell counter (Thermo Fisher Scientific), count cell populations to determine viability;
xv. Removing 20% of obtained cell population for cryopreservation with SYNTH-A-FREEZE® CTS™ (Cell Therapy Systems) from Thermo Fisher Scientific and subsequently cataloguing appropriately while using the remaining 80% population for construct assembly.

Example 3

Example 3 is directed to addition of hypodermis and subdermal fat components to the example of a construct according to an embodiment of the invention. The illustrative component addition example involves:
i. Placing a sterile NUNC® Skin Graft Cell Culture Dish or automated dish already containing the assembled and washed scaffold into a laminar flow hood and washing the scaffold again two times with pulse media prior to adding cells;
ii. Inserting a label on each culture vessel with tracking number;
iii. Transferring around 5×105 to 1×106 mixed SVF cells per dish system and 1×105 adipocytes per dish;
iv. Adding a complete culture medium with or without autologous PRP as dictated by the particular requirements of a situation, to the loading reservoir;
v. Transferring the dishes into an incubator onto slow rocker for 1 hour followed by removal therefrom and resting flat for 48 hours in separate sentinel incubator;
vi. Washing the culture medium after 48 hours, discarding the non-adherent cells, and renewing the complete culture medium. Image with a cell imaging device such as an EVOS® (ThermoFisher Scientific) and store with the designated tracking number.
vii. Every 72 hours replacing the culture medium;
viii. At confluence, washing the culture with Dulbecco's phosphate-buffered saline (DPBS) and replacing the culture media with fresh media.
ix. Placing the epithelial stem cell functional singularity constructs (ESC FSUs) directly on the surface of the mesenchymal stem cell (MSC) construct, adding ESC media to cover both constructs, imaging the same and replacing the construct into the incubator.
x. Changing/replacing the construct media every 48 hours.

Example 4

Example 4 concerns enrichment of the minimally polarized, epithelial stem cell singularity units.
Following Example 1, the MPFUs is placed in pulse rescue media in a 15 ml conical tube and spin/centrifuged into a soft pellet. The material is then subject to the following process of partial digestion:
i. Obtaining a previously aliquoted frozen 10 ml digestion buffer (collagenase and dispase-based), which has been brought to room temperature prior adding to MPFUs;
ii. Adding the digestion solution to the soft pellet of MPFUs and gently mixing, by flicking, the tube to allow MPFUs to distribute throughout the solution;
iii. Placing the tube into 37° C. water bath or dry incubator for 10 minutes;
iv. Removing the tube from the bath/incubator, gently flicking tube and examining the content for string;
v. Having observed string, centrifuging the content into a soft pellet;
vi. Washing the cell pellet in 5-10 mL complete Defined Keratinocyte SFM medium (Keratinocyte-SFM (1×) from ThermoFisher Scientific) and centrifuging into soft pellet again;
vii. Re-suspending the pellet of activated functional singularity units in 5 mL of complete the Keratinocyte-SFM medium; and
viii. Determining the cell density of the units using a COUNTESS® Automated Cell Counter (ThermoFisher Scientific).

Example 5

Example 5 involves adding the epithelial stem cell functional singularities (ESC aFSUs) obtained from Example 4 to a construct/scaffold. The procedure entails:
i. Placing an UPCELL™ Surface Skin Graft Cell Culture Dish already containing an assembled and washed scaffold, and to assure physiologic pH, washing the scaffold twice again with pulse media prior to adding the cells;
ii. Labelling each culture vessel with a unique tracking number;
iii. Transferring ESC aFSUs to the construct via disposable transfer pipette using complete Defined Keratinocyte SFM medium (additional autologous PRP is optional);
iv. Adding the complete culture medium to a select loading reservoir and ensuring complete coverage of the construct;
v. Transferring dishes into the incubator onto slow rocker for 1 hour. Then remove from rocker and allow to remain flat for 48 hours in separate sentinel incubator;
vi. At 48 hours, aspirating the culture medium and adding fresh Keratinocyte SFM culture medium. Imaging the culture with EVOS® and storing the culture with the assigned tracking number. Increasing the gingival fibroblasts (GF) population and viability protein and/or supplementing the PRP if a need is detected at this time.
vii. Replacing the culture medium every 48-72 hours;
viii. Upon achieving confluence, washing the culture with DPBS and replacing the media. Reducing the temperature using temperature based system of the ESC construct scaffolding to facilitate release from the dish;
ix. Placing the ESC directly on the surface of the MSC construct and adding combined media to cover both constructs. Imaging the construct, placing it back into the incubator and changing the construct media every 48 hours.
x. To confirm polarization maintenance, imaging the construct daily and adding an appropriate Cornification (rind forming) medium following confirmation that polarization has been maintained for 48 hours;
xi. Washing the construct twice with pulse media at harvest and replacing the media with a defined transport media using CTS™ STEMPRO® MSC SFM base.

Example 6

Example 6 represents illustrative protocols for quality assurance and construct finalization involving cryopreservation which entails preparation the construct for shipment following defined good manufacturing processes (GMP) for cell therapy applications and include:

i. Obtaining an appropriate volume of SYNTH-A-FREEZE® cryopreservation medium (Thermo Fisher Scientific) and storing the medium at 2° C. to 8° C. until use;

ii. Preparing, harvesting and determining cell density using COUNTESS® Automated Cell Counter prior to centrifugation a desired quantity of cells where typical cell densities for cryopreservation with SYNTH-A-FREEZE® medium are 5×105 to 3×106;

iii. Re-suspending the cell pellet in the pre-determined volume of 2° C. to 8° C. of SYNTH-A-FREEZE® medium;

iv. Immediately dispensing aliquots of the obtained suspension into cryovials according to the manufacturer's specifications;

v. Placing the cryovials into an appropriate cryosystem, such as a MR. FROSTY™ system available from Thermo Fisher Scientific Inc. that maintains freezer temperatures at −80° C.;

vi. Transferring the vials to a liquid nitrogen long-term vapor-phase storage at −200° C. to −125° C.

The described embodiments of the invention have been provided in the forgoing specification. It should be understood by those skilled in the art that many modifications and embodiments of the invention will come to mind to which the invention pertains, having benefit of the teaching presented in the foregoing description and associated drawing. Therefore, it also should understood that the invention is not limited to the specific embodiments disclosed herein, and that many modifications and other embodiments of the invention are intended to be included within the scope of the invention. Moreover, although specific terms are employed herein, they are used only in generic and descriptive sense, and not for the purposes of limiting the description invention.

UTILITY/INDUSTRIAL APPLICABILITY

The invention relates to methods for making and methods for using constructs of micro-aggregate multicellular grafts containing isolated Leucine-rich repeat-containing G-protein coupled Receptor (LGR) expressing cells for the delivery, application, transplantation, implantation, directed seeding, directed migration, directed tracking, in setting, laminating and/or injection of the cellular element generating, regenerating, enhancing and/or healing epithelial systems, glands, hair, nerves, bone, muscle, fat, tendons, blood vessels, fascia, ocular tissues and peptide secreting cellular elements for use in wound therapy applications, tissue engineering, cell therapy applications, regenerative medicine applications, medical/therapeutic applications, tissue healing applications, immune therapy applications, and tissue transplant therapy applications.

I claim:

1. A method, comprising:
   a) separating fat and hypodermal elements from a mammalian tissue specimen ex vivo to provide remaining cutaneous elements containing an epidermal compartment, a dermal compartment, and a follicular compartment;
      b) cutting through the epidermal compartment, the dermal compartment, and the follicular compartment to open the follicular compartment and prepare a cellular micro-aggregate comprising an epidermal segment, a dermal segment, and a segment of the follicular compartment, wherein the segments are interconnected and wherein the segment of the follicular compartment comprises living LGR-expressing stem cells that are exposed;
   c) processing the fat and hypodermal elements to provide a mesenchymal-derived cellular population; and
   d) adding the mesenchymal-derived cellular population to the cellular micro-aggregate to provide a composition, wherein the composition is capable of regenerating functional tissue comprising epidermis, dermis, and appendages when transplanted to a damaged tissue site in a subject in need thereof.

2. The method of claim 1, wherein the living LGR-expressing stem cells comprise LGR4-expressing stem cells, LGR5-expressing stem cells, LGR6-expressing stem cells, or any combination thereof.

3. The method of claim 1, further comprising adding a cornification medium to the composition.

4. The method of claim 1, further comprising cryopreserving the composition.

5. The method of claim 1, wherein the mesenchymal-derived cellular population comprises an adipocyte population, a stromal vascular fraction, or any combination thereof.

6. The method of claim 1, further comprising adding the composition to a delivery substrate selected from scaffolding, matrix, particle, cells, fiber, or any combination thereof.

7. The method of claim 1, further comprising adding enhancing factors to the composition.

8. The method of claim 1, wherein b) comprises cutting through the epidermal compartment, the dermal compartment, and a bulge of the follicular compartment.

9. The method of claim 1, wherein b) comprises segmenting the epidermal compartment, the dermal compartment, and a bulb of the follicular compartment.

10. The method of claim 1, further comprising adding the composition to a pharmaceutically acceptable carrier.

11. A method, comprising applying the composition produced by the method of claim 1 to a select target.

12. The method of claim 11, wherein the select target is selected from a tissue region, a wound, a void, a defective tissue, or any combination thereof.

13. The method of claim 11, wherein the select target is an injury involving single or multiple tissue elements.

14. The method of claim 11, wherein the applying is direct or indirect.

15. The method of claim 11, wherein the applying is direct and a delivery technique is selected from transplantation, implantation, directed seeding, directed migration, directed tracking, in setting, laminating, injection, or combinations thereof.

16. A method comprising:
   a) separating fat and hypodermal elements from a mammalian tissue specimen ex vivo to provide remaining cutaneous elements containing an epidermal compartment, a dermal compartment, and a follicular compartment;
   b) segmenting epidermal compartment, the dermal compartment, and the follicular compartment to open the follicular compartment and prepare an epidermal segment, a dermal segment, and a segment of the follicular compartment, wherein the segments are interconnected and wherein the segment of the follicular compartment comprises living LGR-expressing stem cells that are exposed;
   c) processing the fat and hypodermal elements to provide a mesenchymal-derived cellular population; and d) adding the mesenchymal-derived cellular population to the interconnected segments to provide a composition, wherein the composition is capable of regenerating functional tissue comprising epidermis, dermis, and appendages when transplanted to a damaged tissue site in a subject in need thereof.

17. The method of claim 16, wherein the living LGR-expressing stem cells comprise LGR4-expressing stem cells, LGR5-expressing stem cells, LGR6-expressing stem cells, or any combination thereof.

18. The method of claim 16, further comprising adding a cornification medium to the composition.

19. The method of claim 16, further comprising cryopreserving the composition.

20. The method of claim 16, wherein the mesenchymal-derived cellular population comprises an adipocyte population, a stromal vascular fraction, or any combination thereof.

21. The method of claim 16, further comprising adding the composition to a delivery substrate selected from scaffolding, matrix, particle, cells, fiber, or any combination thereof.

22. The method of claim 16, further comprising adding enhancing factors to the composition.

23. The method of claim 16, further comprising adding the composition to a pharmaceutically acceptable carrier.

24. The method of claim 16, wherein b) comprises cutting through the epidermal compartment, the dermal compartment, and a bulge of the follicular compartment.

25. The method of claim 16, wherein b) comprises segmenting the epidermal compartment, the dermal compartment, and a bulb of the follicular compartment.

26. A method, comprising applying the composition produced by the method of claim 16 to a select target.

27. The method of claim 26, wherein the select target is selected from a tissue region, a wound, a void, a defective tissue, or any combination thereof.

28. The method of claim 26, wherein the select target is an injury involving single or multiple tissue elements.

29. The method of claim 26, wherein the applying is direct or indirect.

30. The method of claim 26, wherein the applying is direct and a delivery technique is selected from transplantation, implantation, directed seeding, directed migration, directed tracking, in setting, laminating, injection, or combinations thereof.

* * * * *